US008158589B2

(12) United States Patent
Dotor Herrerías et al.

(10) Patent No.: US 8,158,589 B2
(45) Date of Patent: Apr. 17, 2012

(54) PEPTIDES WITH THE CAPACITY TO BIND TO TRANSFORMING GROWTH FACTOR β1 (TGF-β1)

(75) Inventors: Javier Dotor Herrerías, Pamplona (ES); Francisco Borrás Cuesta, Pamplona (ES); Esperanza Feijoo Blanco, Madrid (ES)

(73) Assignees: Proyecto Biomedicine Cima, S.L., Pamplona (Navarra) (ES); Digna Biotech, S.L., Pamplona (Navarra) (ES)

( * ) Notice: Subject to any disclaimer, the term of this patent is extended or adjusted under 35 U.S.C. 154(b) by 0 days.

(21) Appl. No.: 12/709,895

(22) Filed: Feb. 22, 2010

(65) Prior Publication Data

US 2010/0222280 A1    Sep. 2, 2010

Related U.S. Application Data

(63) Continuation-in-part of application No. 10/569,012, filed on Aug. 11, 2006, now Pat. No. 7,666,841.

(30) Foreign Application Priority Data

Aug. 22, 2003 (ES) .................................. 200302020

(51) Int. Cl.
*A61K 38/08* (2006.01)
*A61K 38/10* (2006.01)

(52) U.S. Cl. ...................................... 514/21.5; 514/21.6
(58) Field of Classification Search .................. None
See application file for complete search history.

(56) References Cited

U.S. PATENT DOCUMENTS 7,057,013 B1    6/2006    Ezquerro Saenz et al.

FOREIGN PATENT DOCUMENTS

| JP | 08151396 A | 5/1996 |
| WO | 0024782 A2 | 5/2000 |

OTHER PUBLICATIONS

Ishikawa, Dai, et al, GD1α-replica peptides functionally mimic GD1α, an adhesion molecule of metastatic tumor cells,and suppress the tumor metastasis, FEBS Letters, 1998, pp. 20-24, vol. 441.
Dotor, Javier, et al., Identification of peptide inhibitors of transforming growth factor beta 1 using a phage-displayed peptide library, Cytokine (2007) vol. 39, pp. 106-115.

*Primary Examiner* — Marianne P Allen
(74) *Attorney, Agent, or Firm* — Tristan A. Fuierer; Andrew D. Gerschutz; Moore & Van Allen, PLLC

(57) ABSTRACT

The described peptides possess the capacity to bind to Transforming Growth Factor TGF-β1 (TGF-β1), and are potential inhibitors of the biological activity of TGF-β1 through direct binding to this cytokine. These peptides can be used in the treatment of diseases or pathological alterations based on excessive or deregulated TGF-β1 expression, e.g., liver fibrosis, pulmonary fibrosis, corneal fibrosis and haze.

7 Claims, 18 Drawing Sheets

SEQUENCE LISTING

```
<160> NUMBER OF SEQ ID NOS: 53

<210> SEQ ID NO 1
<211> LENGTH: 15
<212> TYPE: PRT
<213> ORGANISM: Artificial sequence
<220> FEATURE:
<223> OTHER INFORMATION: Synthetic Construct

<400> SEQUENCE: 1

Asp Arg Arg Ile Phe Trp Trp Ser Leu Arg Ser Ala Pro Gly Ala
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Synthetic Construct

<400> SEQUENCE: 2

Asp Arg Arg Ile Phe Trp Trp Ser Asn Arg Ser Ala Pro Gly Ala
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: Synthetic Construct

<400> SEQUENCE: 3

Arg Phe Phe Thr Arg Phe Pro Trp His Tyr His Ala Ser Arg Leu
1               5                   10                  15

<210> SEQ ID NO 4
<211> LENGTH: 15
<212> TYPE: PRT
<213> ORGANISM: Artificial sequence
<220> FEATURE:
<223> OTHER INFORMATION: Synthetic Construct

<400> SEQUENCE: 4

Arg Leu Ala His Ser His Arg His Arg Ser His Val Ala Leu Thr
1               5                   10                  15

<210> SEQ ID NO 5
<211> LENGTH: 15
```

```
<212> TYPE: PRT
<213> ORGANISM: Artificial sequence
<220> FEATURE:
<223> OTHER INFORMATION: Synthetic Construct

<400> SEQUENCE: 5

Arg Arg Trp Val Arg Tyr Pro Val His Leu His Ser Pro Ile Val
1               5                   10                  15

<210> SEQ ID NO 6
<211> LENGTH: 15
<212> TYPE: PRT
<213> ORGANISM: Artificial sequence
<220> FEATURE:
<223> OTHER INFORMATION: Synthetic Construct

<400> SEQUENCE: 6

Pro Pro Tyr His Arg Phe Trp Arg Gly His Arg His Ala Val Gln
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: Synthetic Construct

<400> SEQUENCE: 7

His Arg Ile Ser His Phe Ala His Arg Tyr Leu Ala Arg Leu His
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: Synthetic Construct

<400> SEQUENCE: 8

Trp His Trp Arg His Arg Ile Pro Leu Gln Leu Ala Ala Gly Arg
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic Construct

<400> SEQUENCE: 9

Gly Trp His Ser Leu Leu His Ser Arg Tyr His Arg Leu Ala Ala
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Synthetic Construct

<400> SEQUENCE: 10

Phe Val Trp Val Arg Phe His Arg Leu Pro Arg Gln Ile Tyr Thr
1               5                   10                  15

<210> SEQ ID NO 11
<211> LENGTH: 15
<212> TYPE: PRT
<213> ORGANISM: Artificial sequence
```

```
<220> FEATURE:
<223> OTHER INFORMATION: Synthetic Construct

<400> SEQUENCE: 11

Trp His Lys Tyr Phe Leu Arg Arg Pro Leu Ser Val Arg Thr Arg
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Synthetic Construct

<400> SEQUENCE: 12

Trp His Lys Tyr Phe Leu Arg Arg Pro Leu Ser Val Gly Leu Gly
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: Synthetic Construct

<400> SEQUENCE: 13

Arg Lys Trp Phe Leu Gln His Arg Arg Met Pro Val Ser Val Leu
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Synthetic Construct

<400> SEQUENCE: 14

Ser Gly Arg Arg His Leu His Arg His His Ile Phe Ser Leu Pro
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: Synthetic Construct

<400> SEQUENCE: 15

Gly Trp Ile Thr Phe His Arg Arg His His Asp Arg Val Leu Ser
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Synthetic Construct

<400> SEQUENCE: 16

Arg Leu His Gly His Arg Ser His Arg Phe Thr His Val Ala Gln
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: Synthetic Construct
```

```
<400> SEQUENCE: 17

Lys Arg Ile Trp Phe Ile Pro Arg Ser Ser Trp Tyr Glu Arg Ala
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: Synthetic Construct

<400> SEQUENCE: 18

Met Pro Leu Ser Arg Tyr Trp Trp Leu Phe Ser His Arg Pro Arg
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Synthetic Construct

<400> SEQUENCE: 19

Arg His Leu Ser His Phe Lys Trp Leu Arg Ser His Gly Leu Asp
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Synthetic Construct

<400> SEQUENCE: 20

Arg Arg Phe His Phe His Ser Arg Met Val Ala Val Asp Asn Ser
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: Synthetic Construct

<400> SEQUENCE: 21

His Val Arg Leu His His Tyr Leu Arg His Arg Ser Leu Pro Asn
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Synthetic Construct

<400> SEQUENCE: 22

Val Pro Met Ala Leu Asn His Gly Val Tyr Val Met Val Ser Ser
1               5                   10                  15

<210> SEQ ID NO 23
<211> LENGTH: 18
<212> TYPE: DNA
<213> ORGANISM: Artificial sequence
<220> FEATURE:
<223> OTHER INFORMATION: Synthetic Construct

<400> SEQUENCE: 23
```

```
tgaattttct gtatgagg                                                    18
```

<210> SEQ ID NO 24
<211> LENGTH: 14
<212> TYPE: PRT
<213> ORGANISM: Artificial sequence
<220> FEATURE:
<223> OTHER INFORMATION: Synthetic Construct

<400> SEQUENCE: 24

```
Arg Ile Trp Phe Ile Pro Arg Ser Ser Trp Tyr Glu Arg Ala
1               5                   10
```

<210> SEQ ID NO 25
<211> LENGTH: 13
<212> TYPE: PRT
<213> ORGANISM: Artificial sequence
<220> FEATURE:
<223> OTHER INFORMATION: Synthetic Construct

<400> SEQUENCE: 25

```
Arg Ile Trp Phe Ile Pro Arg Ser Ser Trp Tyr Glu Arg
1               5                   10
```

<210> SEQ ID NO 26
<211> LENGTH: 13
<212> TYPE: PRT
<213> ORGANISM: Artificial sequence
<220> FEATURE:
<223> OTHER INFORMATION: Synthetic Construct

<400> SEQUENCE: 26

```
Ile Trp Phe Ile Pro Arg Ser Ser Trp Tyr Glu Arg Ala
1               5                   10
```

<210> SEQ ID NO 27
<211> LENGTH: 11
<212> TYPE: PRT
<213> ORGANISM: Artificial sequence
<220> FEATURE:
<223> OTHER INFORMATION: Synthetic Construct

<400> SEQUENCE: 27

```
Ile Trp Phe Ile Pro Arg Ser Ser Trp Tyr Glu
1               5                   10
```

<210> SEQ ID NO 28
<211> LENGTH: 9
<212> TYPE: PRT
<213> ORGANISM: Artificial sequence
<220> FEATURE:
<223> OTHER INFORMATION: Synthetic Construct

<400> SEQUENCE: 28

```
Trp Phe Ile Pro Arg Ser Ser Trp Tyr
1               5
```

<210> SEQ ID NO 29
<211> LENGTH: 12
<212> TYPE: PRT
<213> ORGANISM: Artificial sequence
<220> FEATURE:
<223> OTHER INFORMATION: Synthetic Construct

<400> SEQUENCE: 29

```
Trp Phe Ile Pro Arg Ser Ser Trp Tyr Glu Arg Ala
1               5                   10
```

<210> SEQ ID NO 30
<211> LENGTH: 11
<212> TYPE: PRT
<213> ORGANISM: Artificial sequence
<220> FEATURE:
<223> OTHER INFORMATION: Synthetic Construct

<400> SEQUENCE: 30

Phe Ile Pro Arg Ser Ser Trp Tyr Glu Arg Ala
1               5                   10

<210> SEQ ID NO 31
<211> LENGTH: 10
<212> TYPE: PRT
<213> ORGANISM: Artificial sequence
<220> FEATURE:
<223> OTHER INFORMATION: Synthetic Construct

<400> SEQUENCE: 31

Ile Pro Arg Ser Ser Trp Tyr Glu Arg Ala
1               5                   10

<210> SEQ ID NO 32
<211> LENGTH: 9
<212> TYPE: PRT
<213> ORGANISM: Artificial sequence
<220> FEATURE:
<223> OTHER INFORMATION: Synthetic Construct

<400> SEQUENCE: 32

Pro Arg Ser Ser Trp Tyr Glu Arg Ala
1               5

<210> SEQ ID NO 33
<211> LENGTH: 14
<212> TYPE: PRT
<213> ORGANISM: Artificial sequence
<220> FEATURE:
<223> OTHER INFORMATION: Synthetic Construct

<400> SEQUENCE: 33

Lys Arg Ile Trp Phe Ile Pro Arg Ser Ser Trp Tyr Glu Arg
1               5                   10

<210> SEQ ID NO 34
<211> LENGTH: 12
<212> TYPE: PRT
<213> ORGANISM: Artificial sequence
<220> FEATURE:
<223> OTHER INFORMATION: Synthetic Construct

<400> SEQUENCE: 34

Lys Arg Ile Trp Phe Ile Pro Arg Ser Ser Trp Tyr
1               5                   10

<210> SEQ ID NO 35
<211> LENGTH: 10
<212> TYPE: PRT
<213> ORGANISM: Artificial sequence
<220> FEATURE:
<223> OTHER INFORMATION: Synthetic Construct

<400> SEQUENCE: 35

Lys Arg Ile Trp Phe Ile Pro Arg Ser Ser
1               5                   10

```
<210> SEQ ID NO 36
<211> LENGTH: 9
<212> TYPE: PRT
<213> ORGANISM: Artificial sequence
<220> FEATURE:
<223> OTHER INFORMATION: Synthetic Construct

<400> SEQUENCE: 36

Lys Arg Ile Trp Phe Ile Pro Arg Ser
1               5

<210> SEQ ID NO 37
<211> LENGTH: 20
<212> TYPE: DNA
<213> ORGANISM: Artificial sequence
<220> FEATURE:
<223> OTHER INFORMATION: Synthetic Construct

<400> SEQUENCE: 37
tttggagaga gcatgaccga                                              20

<210> SEQ ID NO 38
<211> LENGTH: 22
<212> TYPE: DNA
<213> ORGANISM: Artificial sequence
<220> FEATURE:
<223> OTHER INFORMATION: Synthetic Construct

<400> SEQUENCE: 38
tgctgtaggt gaagcgactg tt                                           22

<210> SEQ ID NO 39
<211> LENGTH: 20
<212> TYPE: DNA
<213> ORGANISM: Artificial sequence
<220> FEATURE:
<223> OTHER INFORMATION: Synthetic Construct

<400> SEQUENCE: 39
ctatctatgc tgtggaggag                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic Construct

<400> SEQUENCE: 40
gagtttggtg gtctgttgtg                                              20

<210> SEQ ID NO 41
<211> LENGTH: 23
<212> TYPE: DNA
<213> ORGANISM: Artificial sequence
<220> FEATURE:
<223> OTHER INFORMATION: Synthetic Construct

<400> SEQUENCE: 41
acattgatcg ccctaaagga act                                          23

<210> SEQ ID NO 42
<211> LENGTH: 24
<212> TYPE: DNA
<213> ORGANISM: Artificial sequence
<220> FEATURE:
<223> OTHER INFORMATION: Synthetic Construct
```

```
<400> SEQUENCE: 42
tgtggactgg attccaatca gggg                                           24

<210> SEQ ID NO 43
<211> LENGTH: 24
<212> TYPE: DNA
<213> ORGANISM: Artificial sequence
<220> FEATURE:
<223> OTHER INFORMATION: Synthetic Construct

<400> SEQUENCE: 43
tcaagtggca tagatgtgga agaa                                           24

<210> SEQ ID NO 44
<211> LENGTH: 21
<212> TYPE: DNA
<213> ORGANISM: Artificial sequence
<220> FEATURE:
<223> OTHER INFORMATION: Synthetic Construct

<400> SEQUENCE: 44
tggctctgca ggattttcat g                                              21

<210> SEQ ID NO 45
<211> LENGTH: 21
<212> TYPE: DNA
<213> ORGANISM: Artificial sequence
<220> FEATURE:
<223> OTHER INFORMATION: Synthetic Construct

<400> SEQUENCE: 45
aaagccgctc gcaagagtgc g                                              21

<210> SEQ ID NO 46
<211> LENGTH: 14
<212> TYPE: DNA
<213> ORGANISM: Artificial sequence
<220> FEATURE:
<223> OTHER INFORMATION: Synthetic Construct

<400> SEQUENCE: 46
ctcctgcaaa gcac                                                      14

<210> SEQ ID NO 47
<211> LENGTH: 20
<212> TYPE: DNA
<213> ORGANISM: Artificial sequence
<220> FEATURE:
<223> OTHER INFORMATION: Synthetic Construct

<400> SEQUENCE: 47
tgattagagc caactgcctg                                                20

<210> SEQ ID NO 48
<211> LENGTH: 20
<212> TYPE: DNA
<213> ORGANISM: Artificial sequence
<220> FEATURE:
<223> OTHER INFORMATION: Synthetic Construct

<400> SEQUENCE: 48
ggtatgtctt catgctggtg                                                20

<210> SEQ ID NO 49
<211> LENGTH: 17
<212> TYPE: DNA
```

```
<213> ORGANISM: Artificial sequence
<220> FEATURE:
<223> OTHER INFORMATION: Synthetic Construct

<400> SEQUENCE: 49
agcctcgcct ttgccga                                                    17

<210> SEQ ID NO 50
<211> LENGTH: 15
<212> TYPE: DNA
<213> ORGANISM: Artificial sequence
<220> FEATURE:
<223> OTHER INFORMATION: Synthetic Construct

<400> SEQUENCE: 50
ctggtgcctg gggcg                                                      15

<210> SEQ ID NO 51
<211> LENGTH: 14
<212> TYPE: PRT
<213> ORGANISM: Artificial sequence
<220> FEATURE:
<223> OTHER INFORMATION: Synthetic Construct

<400> SEQUENCE: 51

Thr Ser Leu Asp Ala Ser Ile Ile Trp Ala Met Met Gln Asn
1               5                   10

<210> SEQ ID NO 52
<211> LENGTH: 72
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
```

```
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 52
gccgacgggg ctnnknnknn knnknnknnk nnknnknnkn nknnknnknn knnknnkggg      60
gccgctgggg cc                                                          72

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Lys Arg Ile Trp Phe Ile Pro Arg Ser Ser Trp
1               5                   10
```

PEPTIDES WITH THE CAPACITY TO BIND TO TRANSFORMING GROWTH FACTOR β1 (TGF-β1)

CROSS-REFERENCE TO RELATED APPLICATIONS

This application is a Continuation in Part and claims priority to U.S. patent application Ser. No. 10/569,012, filed on Jul. 7, 2008, now U.S. Pat. No. 7,666,841, which in turn claims priority to PCT International Application No. PCT/ES2004/000320, filed on Jul. 5, 2004, which in turn claims priority to Spanish Patent Application No. P200302020, filed on Aug. 22, 2003, the contents of all are hereby incorporated by reference herein.

FIELD OF THE INVENTION

The invention generally refers to peptides with the capacity to bind to transforming growth factor β1 (TGF-β1), and their applications. In particular, the invention refers to peptides that inhibit the biological activity of TGF-β1 as a result of direct bonding to TGF-β1, and to their use in the treatment of diseases or pathological alterations based on the excessive or deregulated expression of TGF-β1; most particularly, for the treatment of liver fibrosis, pulmonary fibrosis, corneal fibrosis and haze.

BACKGROUND OF THE INVENTION

TGF-β1 is a glycoprotein belonging to a superfamily of structurally related regulatory proteins (cytokines) included within one of the three isoforms described in mammals (TGF-β 1, 2 and 3). The most abundant isoform is TGF-β1, which consists of a 25 kDa homodimer composed of two subunits joined by a disulfide bond. The amino acid sequence of human TGF-β1 has been described by authors such as Derynck K et al., "Human transforming growth factor-beta complementary DNA sequence and expression in normal and transformed cells". Nature 316 (6030), 701-705 (1985).

TGF-β1 is a molecule with a highly preserved sequence in evolutive terms. Although it was originally defined by its capacity to induce adhesion independent of proliferation and morphological changes in rat fibroblasts, subsequent investigations have shown that TGF-β1 is a general inhibitor of proliferation of a broad range of cell types. The molecule is produced by a great variety of cell types and in different tissues during all phases of cell differentiation. It has a large series of biological effects, with the generation of potent and very often opposite effects in relation to development, physiology and immune response. Information on the role of TGF-β1 in liver regeneration and differentiation, and in liver fibrosis, as well as on the effects of the molecule upon the extracellular matrix, can be found in Spanish patent application ES 2146552 A1.

With the purpose of exploring the mechanism of action of TGF-β1, some ten proteins (membrane receptors and extracellular matrix proteins) have been reported to interact with this cytokine.

On the other hand, since many diseases or pathological alterations are associated with excessive or deregulated expression of TGF-β1, e.g., fibrosis associated to organ or tissue function loss, or surgical or esthetic complications, it is of interest to search for products capable of inhibiting the biological activity of TGF-β1—since such products can be potentially used in human or animal therapy to block the pathological consequences of excessive or deregulated TGF-β1 expression.

Several strategies have been used to inhibit the biological activity of TGF-β1 including the use of: (i) specific neutralizing antibodies; (ii) antisense oligonucleotides sequences of the gene encoding TGF-β1 which block its expression; or (iii) soluble receptors for TGF-β1 that act in a way similar to antibodies. The use of antibodies affords total and specific blockage of this cytokine (TGF-β1), though certain side effects are enhanced by both the presence of exogenous immunoglobulins in blood and the effects derived from the systemic blockage of TGF-β1. In addition, immunoglobulin stability over time does not allow short-time control of the blocking activity of this cytokine. Antisense oligonucleotides sequences inhibit TGF-β1 production at gene expression level—a fact that can generate important deregulation of all processes in which this cytokine participates.

Another strategy has recently been developed, based on the use of peptides that inhibit the biological activity of TGF-β1. In this sense, Spanish patent application ES 2146552 A1 describes some synthetic peptides originating from both TGF-β1 and its receptors, or from proteins capable of binding to TGF-β1, and which can be used as inhibitors of the biological activity of TGF-β1.

Illustrative examples of diseases or pathological alterations associated with excessive or deregulated expression of TGF-β1 include liver fibrosis, pulmonary fibrosis, corneal fibrosis and haze.

Liver fibrosis is the excessive accumulation of extracellular matrix (ECM) proteins including collagen that occurs in most types of chronic liver diseases. Advanced liver fibrosis results in cirrhosis, liver failure, and portal hypertension and often requires liver transplantation. Activated hepatic stellate cells, portal fibroblasts, and myofibroblasts of bone marrow origin have been identified as major collagen-producing cells in the injured liver. These cells are activated by fibrogenic cytokines such as TGF-β1, angiotensin II, and leptin. Reversibility of advanced liver fibrosis in patients has been recently documented, which has stimulated researchers to develop antifibrotic drugs. Emerging antifibrotic therapies are aimed at inhibiting the accumulation of fibrogenic cells and/or preventing the deposition of ECM proteins. A review summarizing recent progress in the study of the pathogenesis and diagnosis of liver fibrosis and discusses current antifibrotic strategies can be seen, for example, in Bataller R & Brenner D. A. Liver fibrosis. J Clin Invest. 2005 April; 115(4):1100.

Pulmonary fibrosis (PF) is a progressive lung disorder characterized by accumulation of ECM proteins. Unfortunately, despite its high impact on human health, no effective treatment has been yet developed. Pathogenesis of PF appears to result from a complex interaction between inflammatory cells, fibroblasts and lung parenchymal cells. Inflammatory cells produce profibrotic cytokines which cause fibroblast transformation, proliferation and accumulation of ECM proteins, causing tissue destruction and loss of lung functions. One of the most relevant profibrotic cytokines in PF is TGF-β1, which plays a key role in the synthesis and accumulation of collagen and fibronectin in lungs. This suggests that TGF-β1 inhibition would enhance the efficacy of currently used therapies. Indeed, a protective effect on the development of lung fibrosis has been described in different animal models when using anti-TGF-13 antibodies, decorin or TGF-β1 soluble receptors [Giri S N et al. Effect of antibody to transforming growth factor beta on bleomycin induced accumulation of lung collagen in mice. Thorax 1993; 48:959-966; Giri S N et al. Antifibrotic effect of decorin in a bleomycin hamster model of lung fibrosis. Biochem Pharmacol 1997; 54:1205-1216; Kolb M et al. Transient transgene expression of decorin in the lung reduces the fibrotic response to bleomycin. Am J Respir Crit Care Med 2001; 163:770-777; Wang Q et al. Reduction of bleomycin induced lung fibrosis by transforming growth factor beta soluble receptor in hamsters. Thorax 1999; 54:805-812].

Experimental evidence demonstrates that fibroblasts play a critical role in the wound-healing process and in the development of lung fibrosis. When fibroblasts become activated, they proliferate and may differentiate into myofibroblasts, displaying smooth muscle cell morphology. Different factors secreted by the pulmonary epithelium after damage, including TGF-β1, are involved in these processes inducing enhanced synthesis of ECM proteins, especially collagen and fibronectin. In fact, many in vitro studies have revealed that TGF-β1 promotes myofibroblast differentiation, induces expression of alpha-Smooth Muscle Actin (α-SMA) in lung fibroblasts and enhances the synthesis of the ECM. Interestingly, extra-domain A of fibronectin (EDA-FN), an isoform of fibronectin, is necessary for the induction of the myofibroblast phenotype by TGF-β1 in fibroblast cells. This isoform is de novo expressed during wound healing and plays an essential role in PF. In addition, areas of fibroblastic foci at sites where TGF-β1 is expressed, as well as active ECM products, have been observed in lung tissue sections from patients with idiopathic lung fibrosis.

As mentioned above, the role of TGF-β1 as one of the main fibrosis induction mediators is fully demonstrated in the scientific literature. Fibrosis in the cornea causes loss of transparency, tissue contraction and scar transformation, thus causing corneal haze. The use of both topical steroids and antimetabolites such as mitomycin C as an anti-scarring treatment is currently widespread. However, these drugs can be associated with severe complications.

SUMMARY OF THE INVENTION

The invention in general addresses the problem of seeking new compounds capable to inhibit the biological activity of TGF-β1.

The solution provided by the present invention is based on the fact that the inventors have identified a series of peptides capable not only of binding to TGF-β1 but also of inhibiting the biological activity of TGF-β1 through direct binding to the latter. Some of these peptides have been identified using a technology associated to phage-displayed peptide libraries that allow the identification of peptides, with a typical size in the range of 6 to 15 amino acids, capable of binding with high affinity to TGF-β1, quantifying, subsequently, by in vitro and in vivo assays their capacity to inhibit the biological activity of TGF-β1. Other peptides have been obtained through truncation of peptides previously identified with this technology associated with phage libraries.

Peptides capable of binding to TGF-β1, and in particular those able to inhibit the biological activity of TGF-β1, by its direct bonding to TGF-β1, are potentially useful for the treatment of diseases and pathological alterations associated with excessive or deregulated expression of TGF-β1, for example, liver fibrosis, pulmonary fibrosis, corneal fibrosis and haze. Likewise, peptides capable of binding to TGF-β1 offer a tool for studying the biological role of TGF-β1 (an aspect that remains to be clarified in many areas of the regulation of different biological processes).

Thus, one aspect of this invention relates to peptides capable of binding to TGF-β1. In a particular and preferred embodiment, these peptides are, also, able to inhibit the biological activity of TGF-β1.

In another aspect, the invention relates to a pharmaceutical composition comprising at least one of the mentioned peptides.

In another aspect, the invention relates to the use of said peptides for the preparation of a pharmaceutical composition for the treatment of diseases and pathological alterations associated with excessive or deregulated TGF-β1 expression. Representative examples of such diseases or pathological alterations associated with excessive or deregulated TGF-β1 expression include fibrosis associated with tissue or organ function loss, as well as surgical and/or esthetic complications.

In another aspect, the invention relates to a method of treating liver fibrosis which comprises administering to a subject in need of treatment a therapeutically effective amount of a peptide capable of binding to TGF-β1 and inhibiting the biological activity of TGF-β1. In a particular embodiment, said peptide is a peptide whose amino acid sequence is SEQ ID NO: 17 or a fragment comprising 9, 10, 11, 12, 13, or 14 consecutive amino acid residues of SEQ ID NO:17, or their pharmaceutically acceptable salts, wherein said fragment is characterized by a capacity to bind to TGF-β1. In a preferred embodiment said peptide is a peptide whose amino acid sequence is SEQ ID NO: 17 or SEQ ID NO: 34 (i.e., a fragment comprising 12 consecutive amino acids from the N-terminal end of SEQ ID NO: 17).

In another aspect, the invention relates to a method of treating pulmonary fibrosis which comprises administering to a subject in need of treatment a therapeutically effective amount of a peptide capable of binding to TGF-β1 and inhibiting the biological activity of TGF-β1. In a particular embodiment, said peptide is a peptide whose amino acid sequence is SEQ ID NO: 17 or a fragment comprising 9, 10, 11, 12, 13, or 14 consecutive amino acid residues of SEQ ID NO:17, or their pharmaceutically acceptable salts, wherein said fragment is characterized by a capacity to bind to TGF-β1. In a preferred embodiment said peptide is a peptide whose amino acid sequence is SEQ ID NO: 17.

In another aspect, the invention relates to a method of treating corneal fibrosis which comprises administering to a subject in need of treatment a therapeutically effective amount of a peptide capable of binding to TGF-β1 and inhibiting the biological activity of TGF-β1. In a particular embodiment, said peptide is a peptide whose amino acid sequence is SEQ ID NO: 51, SEQ ID NO: 17 or a fragment comprising 9, 10, 11, 12, 13, or 14 consecutive amino acid residues of SEQ ID NO:17, or their pharmaceutically acceptable salts, wherein said fragment is characterized by a capacity to bind to TGF-β1. In a preferred embodiment said peptide is a peptide whose amino acid sequence is SEQ ID NO: 17 or SEQ ID NO: 51.

In another aspect, the invention relates to a method of treating corneal haze which comprises administering to a subject in need of treatment a therapeutically effective amount of a peptide capable of binding to TGF-β1 and inhibiting the biological activity of TGF-β1. In a particular embodiment, said peptide is a peptide whose amino acid sequence is SEQ ID NO: 51, SEQ ID NO: 17 or a fragment comprising 9, 10, 11, 12, 13, or 14 consecutive amino acid residues of SEQ ID NO:17, or their pharmaceutically acceptable salts, wherein said fragment is characterized by a capacity to bind to TGF-β1. In a preferred embodiment said peptide is a peptide whose amino acid sequence is SEQ ID NO: 51 or SEQ ID NO: 17.

In another aspect, the invention relates to DNA sequences that encode said peptides.

In another aspect, the invention relates to a DNA construct comprising a sequence of DNA that encodes a peptide provided by this invention.

In another aspect, the invention relates to a vector comprising said DNA sequence or DNA construct.

In another aspect, the invention relates to a host cell, such as a transformed host cell, that comprises said DNA construct or vector.

In another aspect, the invention relates to a process for producing a peptide provided by this invention which comprises culturing said host cells under conditions allowing expression of said peptide, and, if desired, recovering the peptide obtained.

In another aspect, the invention relates to the use of said DNA sequences and DNA constructs in the manufacture of vectors and cells for the treatment by gene therapy techniques of diseases and pathological alterations associated with excessive or deregulated TGF-β1 expression.

BRIEF DESCRIPTION OF THE FIGURES

FIG. 15 shows the evolution of corneal haze after the application of p17, wherein:

*** p<0.001; control vs. p17 in the fifth week highly significant;

††† p<0.001; the control at the fifth week vs. the control at day 0 highly significant; and ### p<0.001; the one treated at the fifth week vs. the one treated at day 0 highly significant.

Figure 16:
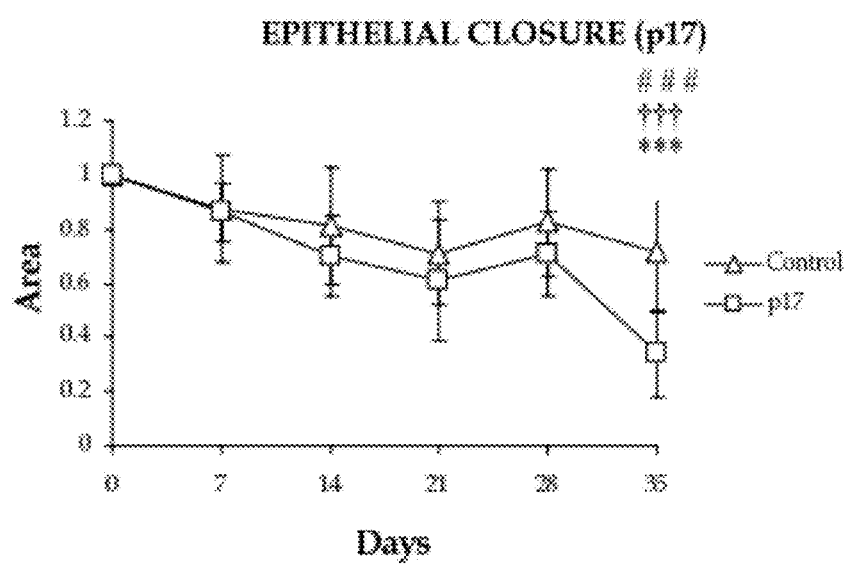

FIG. 16 shows the evolution of the epithelial closure after the application of p17, wherein:

** p<0.01; control vs. p17 in the fifth week very significant;

†† p<0.01; the control at the fifth week vs. the control at day 0 very significant; and

# # p<0.001; the one treated at the fifth week vs. the one treated at day 0 highly significant.

Figure 17:
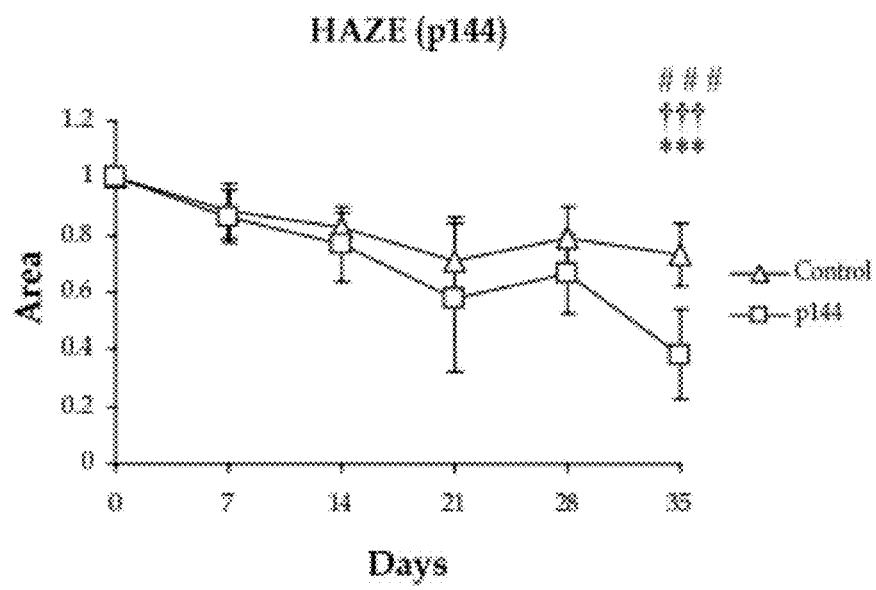

FIG. 17 shows the evolution of corneal haze after the application of p144, wherein:

*** p<0.001; control vs. p17 in the fifth week highly significant;

* p<0.05; control vs. p17 in the second and fourth week significant;

††† p<0.001; the control at the fifth week vs. the control at day 0 highly significant; and

# # p<0.001; the one treated at the fifth week vs. the one treated at day 0 highly significant.

Figure 18:
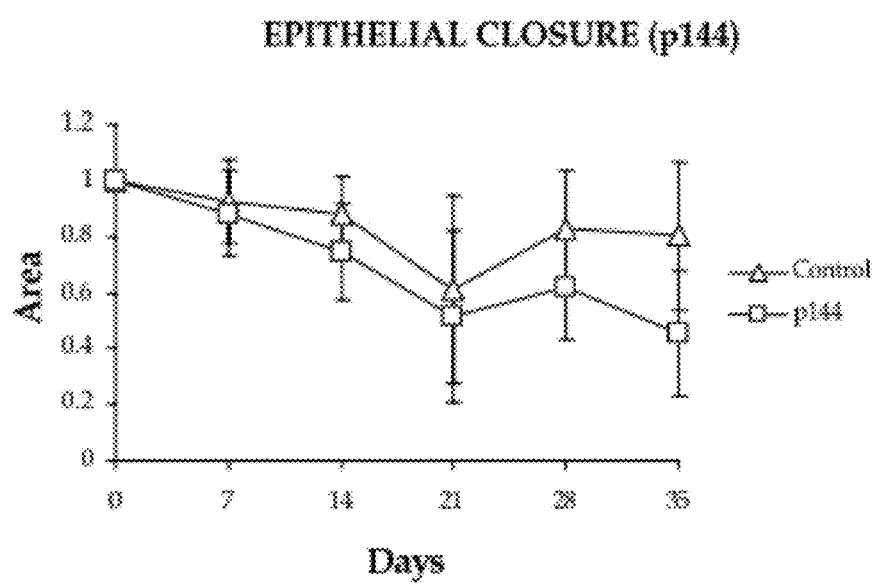

FIG. 18 shows the evolution of the epithelial closure after the application of p144, wherein:

*** p<0.001; control vs. p17 in the fifth week highly significant;

p<0.05; control vs. p17 in the fourth week significant;

†† p<0.01; the control at the fifth week vs. the control at day 0 very significant; and

# # p<0.001; the one treated at the fifth week vs. the one treated at day 0 highly significant.

Figure 19:
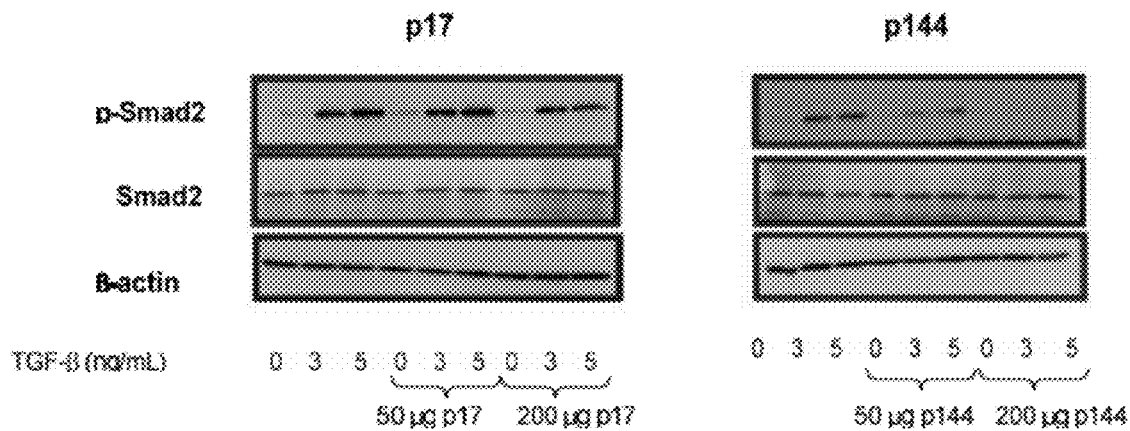

FIG. 19 shows the results of a Western Blot against p-Smad 2, total Smad2 and β-actin (loading control) of p17 and p144.

Figure 20:
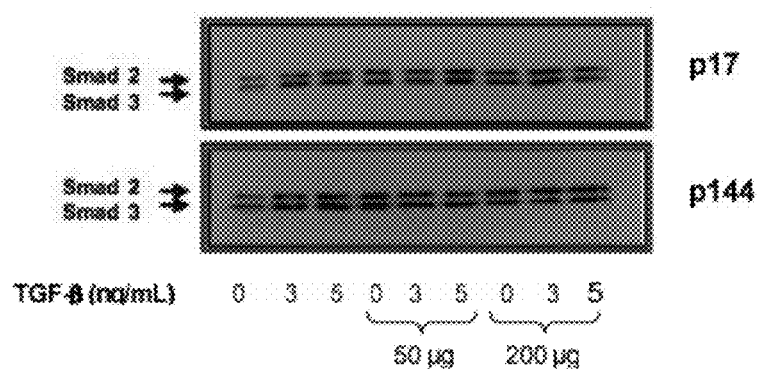

FIG. 20 shows the results of a Western Blot against Smad2/3 in rabbit corneal fibroblasts.

Figure 21:
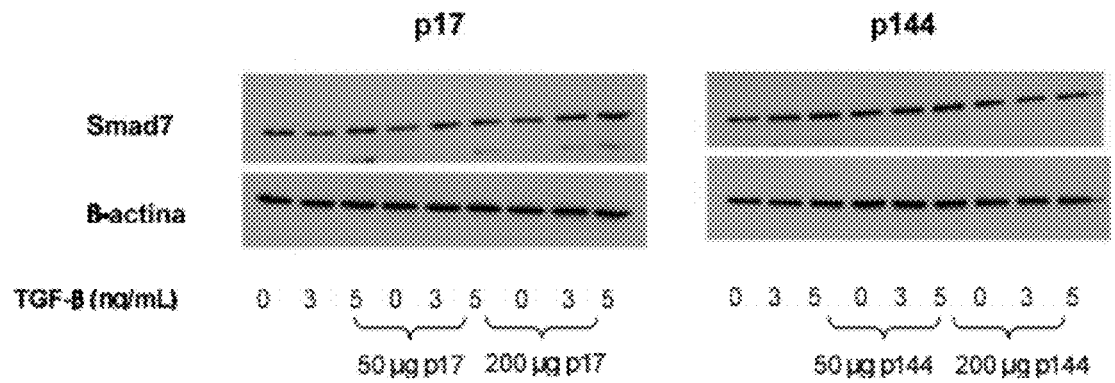

FIG. 21 shows the results of a Western Blot against Smad7 in rabbit corneal fibroblasts treated with TGF-13 with p17 and p144.

Figure 22:
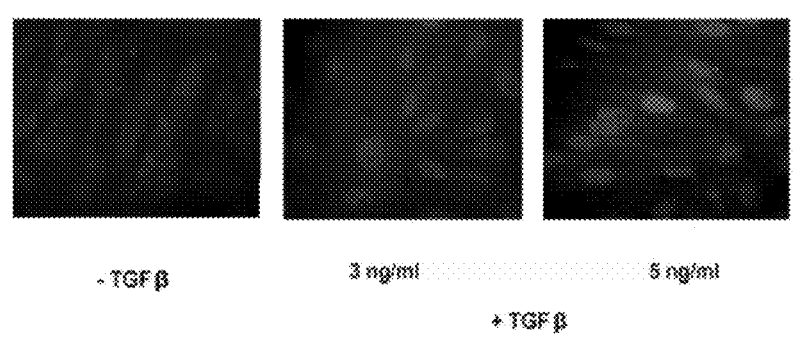

FIG. 22 shows the results of the immunofluorescence studies for p-Smad2 on rabbit corneal fibroblasts without treatment with TGF-β1 and after treatment with 3 ng/ml and 5 ng/ml of TGF-β1.

Figure 23:
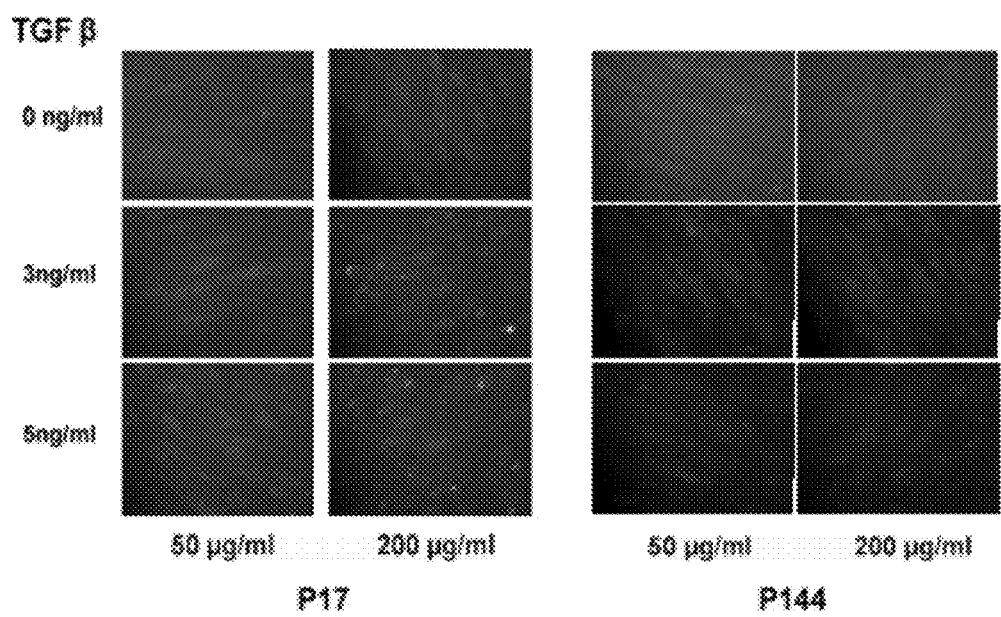

FIG. 23 shows the results of the immunofluorescence studies for p-Smad2 on rabbit corneal fibroblasts without treatment with TGF-β1 and p17 or p144 and after the treatment with different concentrations thereof.

DETAILED DESCRIPTION OF THE INVENTION

In an aspect, the invention relates to a peptide, henceforth referred to as the peptide of the invention, whose amino acid sequence comprises between 3 and 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, and their pharmaceutically acceptable salts.

The peptides of the invention are able to bind to TGF-β1. Some of these peptides are capable of inhibiting the biological activity of TGF-β1 in vitro and/or in vivo.

The capacity of the peptides of the invention to bind to TGF-β1 can be assessed by any appropriate method that allows determination of bonding between two molecules, for example, by means of an affinity assay which comprises placing TGF-β1 in contact with the testing peptide under conditions that allow bonding of the peptide to TGF-β1; and evaluating the bonding between the peptide and TGF-β1. In a particular embodiment, this affinity assay can be performed using radioactively labeled TGF-β1, e.g., human $^{125}$I-TGF-β1, as is described in ES 2146552 A1. Alternatively, the testing peptide can be the labeled component. In general, this kind of affinity assays involves placing TGF-β1 (for example, immobilized on a plate blocked with streptavidin) in contact with the testing peptide whose affinity is to be determined, and, after incubating for an appropriate incubation period of time, analysing the bonding of the peptide to TGF-β1. The peptides with low affinity for TGF-β1 are eliminated by washings, while the peptides with a high affinity remain bound to TGF-β1 and can be freed by breaking the molecular interactions between the two molecules (e.g., by lowering pH). By testing the peptide against different concentrations of TGF-β1, or viceversa, an idea can be gained of the affinity of the testing peptide for TGF-β1. The capacity of the peptides of the invention to inhibit the biological activity of TGF-β1 in vitro can be evaluated and, if desired, quantified by an Mv-1-Lu cell line growth inhibition test, a cell line derived from mink lung epithelium, the proliferation of which is inhibited by TGF-β1 (see Example 2).

The capacity of the peptides of the invention to inhibit the biological activity of TGF-β1 in vivo can be evaluated and, if desired, quantified by testing in an animal model of acute liver damage induced for example by the administration of carbon tetrachloride ($CCl_4$) (see Example 3). As it is known, acute liver damage generates a cascade of effects and physiological responses including an increase in the levels of TGF-β1, which in turn is responsible (among other effects) for the expression of type I collagen gene. Additional tests for assessing the capacity of a peptide to inhibit the biological activity of TGF-β1 in vivo include tests based on the use of an animal model of pulmonary fibrosis (e.g., bleomycin-induced pulmonary fibrosis), as described in Example 5, or the use of an animal model of corneal fibrosis (e.g., NaOH-induced corneal fibrosis), as described in Example 6.

Within the scope of this invention are the pharmaceutically acceptable salts of the peptide of the invention. The term "pharmaceutically acceptable salts" includes those habitually used to form metal salts or acid addition salts. The nature of the salt is not a critical consideration, provided it is pharmaceutically acceptable. The pharmaceutically acceptable salts of the peptide of the invention can be obtained from acids or bases (organic or inorganic), based on conventional methods that are well known by the technicians in the field. Illustrative, non-limitative examples of free acids suitable for use in the present invention include hydrochloric acid, bromic acid, sulfuric acid, and phosphoric acid, citric acid, acetic acid, lactic acid, tartaric acid, fumaric acid, formic acid, propionic acid, oxalic acid, trifluoroacetic acid, methane sulfonic acid, benzene sulfonic acid, maleic acid, benzoic acid, gluconic acid, glycolic acid, succinic acid, 4-morpholine ethane sulfonic acid, camphorsulfonic acid, 4-nitrobenzene sulfonic acid, hydroxy-O-sulfonic acid, 4-toluene sulfonic acid, galacturonic acid, embonic acid, glutamic acid, and aspartic acid.

In a particular embodiment, the invention provides a peptide comprising 3, 4, 5, 6, 7, 8, 9, 10, 11, 12, 13, 14 or 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, and their pharmaceutically acceptable salts. In a preferred embodiment, the invention provides a peptide comprising 9, 10, 11, 12, 13, 14 or 15 consecutive amino acid residues of a sequence of amino acids selected from SEQ ID NO: 3, SEQ ID NO: 4, SEQ ID NO: 6, SEQ ID NO: 11, SEQ ID NO: 13, SEQ ID NO: 14, SEQ ID NO: 17 and SEQ ID NO: 18, and their pharmaceutically acceptable salts.

In another particular embodiment, the invention provides a peptide selected from the group formed by the peptides identified by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, and their pharmaceutically acceptable salts. In a preferred embodiment, the invention provides a peptide whose amino acid sequence is selected from the group consisting of SEQ ID NO: 3, SEQ ID NO: 4, SEQ ID NO: 6, SEQ ID NO: 11, SEQ ID NO: 13, SEQ ID NO: 14, SEQ ID NO: 17 and SEQ ID NO: 18, and their pharmaceutically acceptable salts, preferably, the peptide whose amino acid sequence is SEQ ID NO: 17.

In another particular embodiment, the invention provides a peptide comprising 9, 10, 11, 12, 13, or 14 consecutive amino acid residues of SEQ ID NO: 17 and their pharmaceutically acceptable salts, wherein said fragment is characterized by a capacity to bind to TGF-β1. Thus, in a particular embodiment, the invention provides a peptide selected from the group formed by the peptides identified by SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, and their pharmaceutically acceptable salts. These peptides comprise between 9 and 14 consecutive amino acid residues of the sequence of amino acids of the peptide identified by SEQ ID NO: 17, and have been obtained by truncation of said peptide (Example 4). In a preferred embodiment, the invention provides a peptide whose amino acid sequence is selected from the group consisting of SEQ ID NO: 33 or SEQ ID NO: 34, and their pharmaceutically acceptable salts.

In another particular embodiment, the invention provides a peptide selected from the group formed by the peptides identified by SEQ ID NO: 2, SEQ ID NO: 3, SEQ ID NO: 4, SEQ ID NO: 6, SEQ ID NO: 11, SEQ ID NO: 13, SEQ ID NO: 14, SEQ ID NO: 17, SEQ ID NO: 18, SEQ ID NO: 33 and SEQ ID NO: 34, and their pharmaceutically acceptable salts. The peptides identified by SEQ ID NO: 4, SEQ ID NO: 6, SEQ ID NO: 11, SEQ ID NO: 13, SEQ ID NO: 14 and SEQ ID NO: 17, show an inhibitory capacity of the biological activity of TGF-β1, both in vitro and in vivo; the peptide identified by SEQ ID NO: 2 shows only inhibitory activity of the biological activity of TGF-β1 in vivo; while the peptides identified by SEQ ID NO: 3 and SEQ ID NO: 18 show only inhibitory activity of the biological activity of TGF-β1 in vitro. The peptides identified by SEQ ID NO: 33 and SEQ ID NO: 34 show inhibitory activity of the biological activity of TGF-β1 in vitro.

For the initial identification of peptides with the capacity of binding to TGF-β1 use has been made of the technology involving phage-displayed peptide libraries that allow determining peptides with high binding affinity for TGF-β1 and, subsequently, quantifying in vitro and in vivo their capacity to inhibit the biological activity of TGF-β1. The sequence of said peptides that bind to TGF-β1, inhibiting the biological activity of TGF-β1 in vitro or in vivo, can be deduced from the corresponding DNA sequence after various "biopanning" cycles (generally 3). The use of phage-displayed peptide libraries to identify inhibitors of certain products has been described, for example, by Chirinos-Rojas C. L. et al., in Immunology, 1999, Jan. 96(1): 109-113; McConnell S. J., et al., in Gene 1994, Dec. 30, 151 (1-2): 115-118; or Smith G. P., Science, 1985, Jun. 14, 228 (4705): 1315-1317.

Thus, the invention provides a method for identifying peptides capable of binding to TGF-β1, which comprises:
(i) using a phage-displayed peptide library comprising a plurality of filamentous phages, the genome of each one containing a nucleotide sequence encoding a different peptide linked to the gene encoding a phage envelope protein (thereby each phage contains a different peptide genetically fused to a protein of the phage envelope);
(ii) selecting, via an affinity assay, the phages containing the peptides that bind with increased affinity to TGF-β1; and
(iii) determining the sequence of the peptides that bind to TGF-β1, based on the corresponding DNA sequences inserted in the phages selected in step (ii) and which encode said peptides that bind to TGF-β1.

In a particular embodiment, in order to obtain 15-aa peptides capable of binding with high affinity to TGF-β1, and also with an eventual inhibitory activity upon the biological activity of the mentioned cytokine, use was made of a phage-displayed peptide library comprising a plurality of filamentous bacteriophages (M13), each one containing a different 15-aa peptide genetically fused to a protein of the phage envelope, in this case bond to the N-terminal end of the envelope protein pIII. In this way the phage presents a surface with a 15-aa peptide in each one of the 5 surface protein molecules, while the DNA encoding the mentioned peptide sequence is contained within the phage. In the phage libraries the sequence encoding the peptide originates from a sequence degenerated in each one of the 15 positions with the 20 natural amino acids, thus allowing the presentation of $1.1 \times 10^{12}$ possible sequences of 15 amino acids in different phages. The physical ratio, 1:1, between the peptide sequence and the DNA encoding it within the bacteriophage allows the selection (from among a broad range of variants) of those sequences that specifically bind to TGF-β1. This process is carried out via an affinity assay.

In a particular embodiment, the mentioned affinity assay consists in an in vitro selection protocol known as "biopanning". In brief, this technique involves the incubation of a set of phages representative in practical terms of all the variants of 15-aa peptides (in this case) in a plate blocked with streptavidin and to which biotinylated TGF-β1 is added. The biotinylated TGF-β1 is thus anchored to the plate through the biotin-streptavidin bond thus being correctly displayed for its interaction of TGF-β1 with the peptides carried by the phages. Following incubation, the unbound phages are eliminated by washings, and the specifically bound phages are then specifically eluted by lowering the pH, a procedure that breaks the molecular interactions between TGF-β1 and the peptides presented by the phages. The eluted phages are then amplified via infection in a bacterial strain. The procedure is repeated 3 cycles, so that an enrichment in the content of phages which specifically bind, and with high affinity, to TGF-β1 is achieved. The concentration of biotinylated TGF-β1 used to block the plates is gradually reduced in each cycle, e.g., from 2.5 to 0.01, and finally to 0.001 μg/ml. Thus, at the end of the process, phages which have been selected by their affinity to TGF-β1 are sequenced using primers. This allows obtaining the sequence of the peptides presented by the phages.

Example 1 shows the selection of peptides that bind to TGF-β1 via phage libraries, "biopanning" selection, and sequencing of the peptides that bind with high affinity to TGF-β1.

The invention also provides a method for the identification of peptides capable of binding to TGF-β1 which comprises truncation of the peptides that are able to bind to TGF-β1, followed by testing the capacity of these truncated peptides to bind to TGF-β1. The truncated peptides can be obtained by any conventional method, such as for example chemical synthesis (in view of their size) of the peptide versions truncated at the N-terminal or C-terminal ends. The capacity of these truncated peptides to bind to TGF-β1 can be determined using any appropriate method to characterize binding between two molecules, e.g., an affinity assay, which involves placing TGF-β1 in contact with the testing peptide under conditions allowing binding of the mentioned peptide to TGF-β1 and evaluating the binding of the peptide to TGF-β1, as it has been mentioned above. Likewise, the capacity of these truncated peptides to inhibit the biological activity of TGF-β1 in vitro and/or in vivo can be tested by any of the methods mentioned in this description.

Due to the role played by TGF-β1 in many biological processes, a consequence of the TGF-β1 inhibitory activity of the peptides of the invention has to do with the potential development of a family of drugs for the treatment of diseases and pathological alterations associated with excessive or deregulated TGF-β1 expression, since such peptides can block the damage-induced by excessive or deregulated expression of this cytokine.

The peptides of the invention therefore can be used in the treatment of diseases or pathological alterations associated to excessive or deregulated TGF-β1 expression, such as: (i) fibrosis associated to organ or tissue function loss, e.g., pulmonary fibrosis, liver fibrosis (cirrhosis), renal fibrosis, corneal fibrosis, etc.; and (ii) surgical and/or esthetic complications, e.g., fibrosis associated to skin and peritoneal surgery, fibrosis associated with burns, osteoarticular fibrosis, keloids, etc.

Thus, in another aspect, the invention relates to a pharmaceutical composition comprising a therapeutically effective amount of a peptide of the invention together with at least one pharmaceutically acceptable excipient. The pharmaceutical composition provided by this invention can contain one or more peptides of the invention, optionally in combination with one or more alternative TGF-β1 inhibiting compounds; illustrative, non-limitative examples of TGF-β1 inhibiting compounds include peptides, other than the peptides of the invention, capable of inhibiting the biological activity of TGF-β1, e.g., peptides disclosed in ES 2146552, preferably the peptide identified as P144, whose amino acid sequence is SEQ ID NO: 51. This pharmaceutical composition is useful for administration and/or application to the human or animal body (preferably in the former).

The use of peptides such as those of the present invention, instead of antibodies or antisense oligonucleotides sequences, offers many advantages, since these are small molecules with higher diffusion potential and a shorter half-life. The peptides can exhibit high affinity for TGF-β1, though they degrade faster than antibodies, nevertheless, the side effects may be controlled by dosage. Vehiculization of the peptides to target organs and tissues is also easier compared with other types of compounds.

The peptides of the invention can be administered to treat diseases and pathological alterations associated with excessive or deregulated TGF-β1 expression via any means that place the peptide of the invention in contact with its action site or target within the human or animal body. The amount of peptide, derivative or pharmaceutically acceptable salt that can be present in the pharmaceutical composition provided by this invention can vary over a considerable range. By illustrative, the pharmaceutical composition of the invention can contain, for example, from about 1% to about 99%, preferably from about 10% to about 80%, most preferably from about 20% to about 60%, of the active ingredients (i.e., peptide or peptides of the invention and, optionally, other TGF-β1 inhibiting compounds).

The dosage indicated to treat a disease or pathological alteration associated with excessive or deregulated TGF-β1 expression using the peptides and/or pharmaceutical compositions of the invention will depend on numerous factors—including patient age, condition, the severity of the background disorder or pathological alteration, and the route and frequency of administration of the invention peptide involved. Thus, the pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable excipient or excipients in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy—Gennaro ed. 20th edition, Williams & Wilkins PA, USA (2000).

The pharmaceutical compositions containing the peptides of the invention can be formulated in any form of administration, e.g., solid or liquid, and can be administered via any appropriate route of administration. As used herein "route of administration" refers to any administration pathway known in the art, including but not limited to aerosol, nasal, ophthalmic, oral, parenteral, rectal, topical, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the pharmaceutical compositions of the invention may be in the form of solutions or suspensions for infusion or for injection, or as lyophilized powders. To this effect, pharmaceutically acceptable excipients needed for the formulation of the desired administration form must be included, such as for example ointments (lipogels, hydrogels, etc.), eyedrops, nebulization aerosols, injectable solutions, osmotic pump systems, etc. "Pharmaceutically acceptable excipient" means a vehicle or excipient that is involved in carrying or transporting a compound of interest from one tissue, organ, or portion of the body to another tissue, organ, or portion of the body, and that is useful in preparing a pharmaceutical composition that is generally safe, non-toxic, and desirable; the term includes excipients that are acceptable for veterinary use as well as for human pharmaceutical use. Such excipients may be solid, liquid, semisolid, or, in the case of an aerosol composition, gaseous, e.g., liquid or solid fillers, diluents, solvents, encapsulating materials, or a combination thereof. Each component must be "pharmaceutically acceptable", i.e., it must be compatible with the other ingredients of the formulation and must also be suitable for use in contact with any tissues or organs with which it may come in contact, meaning that it must not carry a risk of toxicity, irritation, allergic response, immunogenicity, or any other complication that excessively outweighs its therapeutic benefits. The pharmaceutical compositions of the invention may be made following the conventional techniques of pharmacy involving milling, mixing, granulation, and compressing, when necessary, for tablet forms, or milling, mixing and filling for hard gelatin capsule forms. When a liquid vehicle is used, the preparation will be in the form of a syrup, elixir, emulsion or an aqueous or non-aqueous suspension. A review of the different drug dosage forms and of the excipients required to the effect can be found, for example, in the publication "Tratado de Farmacia Galénica", C. Faulí i Trillo, 1993, Luzán 5, S.A. Ediciones, Madrid.

The use of peptides of the invention in the manufacture of the mentioned pharmaceutical composition constitutes an additional aspect of this invention. Thus, in another aspect, the invention relates to the use of a peptide of the invention in the manufacture of a pharmaceutical composition for the treatment of diseases or pathological alterations associated with excessive or deregulated TGF-β1 expression, such as fibrosis associated with organ or tissue function loss, e.g., pulmonary fibrosis, liver fibrosis (cirrhosis), renal fibrosis, corneal fibrosis, etc.; and surgical and/or esthetic complications, e.g., fibrosis associated to skin and peritoneal surgery, fibrosis associated with burns, osteoarticular fibrosis, keloids, etc.

As used herein, "treatment", "treat" or "treating" refer to both therapeutic treatment and prophylactic or preventative measures, wherein the object is to prevent or slow down (lessen) the targeted pathologic condition, disease or disorder even if the treatment is ultimately unsuccessful. Those in need of treatment may include those already with the disorder as well as those prone to have the disorder or those in whom the disorder is to be prevented.

Studies performed by the inventors have shown the capacity of the peptides of the invention to inhibit the biological activity of TGF-β1 in vivo in an animal model of acute liver damage induced by the administration of carbon tetrachloride ($CCl_4$), as shown in Example 3 and Dotor J. et al., "Identification of peptide inhibitors of transforming growth factor type 1 using a phage-displayed peptide library". Cytokine 39 (2007):106-115, wherein it is shown that peptides whose amino acid sequence is SEQ ID NO: 17 or SEQ ID NO: 34 are capable of inhibiting the expression of collagen type I mRNA. As it is known, acute liver damage generates a cascade of effects and physiological responses including an increase in the levels of TGF-β1, which in turn is responsible (among other effects) for the expression of type I collagen gene.

Thus, in another aspect, the invention relates to a method of treating liver fibrosis which comprises administering to a subject in need of treatment a therapeutically effective amount of a peptide capable of binding to TGF-β1 and inhibiting the biological activity of TGF-β1, or a pharmaceutically acceptable salt thereof. In a particular embodiment, said peptide comprises 9, 10, 11, 12, 13, 14 or 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22. In another particular embodiment, said peptide is a peptide comprising 9, 10, 11, 12, 13, 14 or 15 consecutive amino acid residues of a sequence of amino acids selected from SEQ ID NO: 3, SEQ ID NO: 4, SEQ ID NO: 6, SEQ ID NO: 11, SEQ ID NO: 13, SEQ ID NO: 14, SEQ ID NO: 17 and SEQ ID NO: 18, or a pharmaceutically acceptable salt thereof. In a preferred embodiment, said peptide is selected from the group consisting of: SEQ ID NO: 17; a peptide comprising 9, 10, 11, 12, 13, or 14 consecutive amino acid residues of SEQ ID NO: 17; and their pharmaceutically acceptable salts, wherein said fragment is characterized by a capacity to bind to TGF-β1. In a preferred embodiment, said peptide is a peptide whose amino acid sequence is SEQ ID NO: 17, or a pharmaceutically acceptable salt thereof. In another preferred embodiment, said peptide is a peptide whose amino acid sequence comprises 9, 10, 11, 12, 13, or 14 consecutive amino acid residues of SEQ ID NO:17, or their pharmaceutically acceptable salts, wherein said peptide has the capacity to bind to TGF-β1, such as a peptide selected from the group formed by the peptides identified by SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, preferably a peptide whose amino acid sequence is SEQ ID NO: 33 or SEQ ID NO: 34. Thus, in a more preferred embodiment, said peptide is a peptide whose amino acid sequence is selected from the group consisting of SEQ ID NO: 17, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, preferably a peptide whose amino acid sequence is SEQ ID NO: 17 or SEQ ID NO: 34.

Further, as it is well-known, pulmonary fibrosis encompasses several respiratory diseases characterized by epithelial cell injury, inflammation and fibrosis. TGF-β1 is one of the main profibrogenic cytokines involved in the pathogenesis of lung fibrosis. It induces fibroblast differentiation into myofibroblasts, which produce high levels of collagen and concomitantly loss of lung elasticity and reduction of the respiratory function. Example 5 shows the effects of the peptide whose amino acid sequence is SEQ ID NO: 17 (P17) on the differentiation of fibroblasts (IMR-90 lung fibroblasts) into myofibroblasts in vitro, and on the development of bleomycin-induced pulmonary fibrosis in mice. It has been found that in IMR-90 cells, P17 inhibited TGF-β1-induced expression of connective tissue growth factor and α-smooth muscle actin (α-SMA). In vivo, treatment of mice with P17 two days after bleomycin administration decreased lung fibrosis, areas of myofibroblast-like cells and lymphocyte infiltrate. P17 also reduced mRNA expression of collagen type I, fibronectin and the fibronectin splice isoform EDA in the lung, and increased the expression of IFN-γ mRNA. Finally, therapeutic treatment with P17 in mice with already established fibrosis was able to significantly attenuate the progression of lung fibrosis. Therefore, these results suggest that P17 may be useful in the treatment of pulmonary fibrosis.

Therefore, in another aspect, the invention relates to a method of treating pulmonary fibrosis which comprises administering to a subject in need of treatment a therapeutically effective amount of a peptide capable of binding to TGF-β1 and inhibiting the biological activity of TGF-β1, or a pharmaceutically acceptable salt thereof. In a particular embodiment, said peptide comprises 9, 10, 11, 12, 13, 14 or 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22. In another particular embodiment, said peptide is a peptide comprising 9, 10, 11, 12, 13, 14 or 15 consecutive amino acid residues of a sequence of amino acids selected from SEQ ID NO: 3, SEQ ID NO: 4, SEQ ID NO: 6, SEQ ID NO: 11, SEQ ID NO: 13, SEQ ID NO: 14, SEQ ID NO: 17 and SEQ ID NO: 18, or a pharmaceutically acceptable salt thereof. In a preferred embodiment, said peptide is selected from the group consisting of: SEQ ID NO: 17; a peptide comprising 9, 10, 11, 12, 13, or 14 consecutive amino acid residues of SEQ ID NO: 17; and their pharmaceutically acceptable salts, wherein said fragment is characterized by a capacity to bind to TGF-β1. In a preferred embodiment, said peptide is a peptide whose amino acid sequence is SEQ ID NO: 17, or a pharmaceutically acceptable salt thereof. In another preferred embodiment, said peptide is a peptide whose amino acid sequence comprises 9, 10, 11, 12, 13, or 14 consecutive amino acid residues of SEQ ID NO:17, or their pharmaceutically acceptable salts, wherein said peptide has the capacity to bind to TGF-β1, such as a peptide selected from the group formed by the peptides identified by SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, preferably a peptide whose amino acid sequence is SEQ ID NO: 33 or SEQ ID NO: 34. Thus, in a more preferred embodiment, said peptide is a peptide whose amino acid sequence is selected from the group consisting of SEQ ID NO: 17, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, preferably a peptide whose amino acid sequence is SEQ ID NO: 17.

The role of TGF-β1 as one of the main fibrosis induction mediators is known and has been broadly demonstrated. Fibrosis in the cornea (corneal fibrosis) causes loss of transparency, tissue contraction and scar transformation, thus causing corneal haze. The use of both topical steroids and antimetabolites such as mitomycin C as an anti-scarring treatment is currently widespread. However, these drugs can be associated with severe complications. Example 6 shows that two TGF-β1 inhibitor peptides [SEQ ID NO: 17 and SEQ ID NO: 51] are capable of completely or partially reducing corneal fibrosis and haze induced by chemical attack.

Therefore, in another aspect, the invention relates to a method of treating corneal fibrosis which comprises administering to a subject in need of treatment a therapeutically effective amount of a peptide capable of binding to TGF-β1 and inhibiting the biological activity of TGF-β1, or a pharmaceutically acceptable salt thereof. In a particular embodiment, said peptide is a peptide whose amino acid sequence comprises SEQ ID NO: 51, a peptide capable to bind to TGF-β1 and inhibit its biological activity, or a pharmaceutically acceptable salt thereof. In another particular embodiment, said peptide comprises 9, 10, 11, 12, 13, 14 or 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22. In another particular embodiment, said peptide is a peptide comprising 9, 10, 11, 12, 13, 14 or 15 consecutive amino acid residues of a sequence of amino acids selected from SEQ ID NO: 3, SEQ ID NO: 4, SEQ ID NO: 6, SEQ ID NO: 11, SEQ ID NO: 13, SEQ ID NO: 14, SEQ ID NO: 17 and SEQ ID NO: 18, or a pharmaceutically acceptable salt thereof. In a preferred embodiment, said peptide is a peptide selected from the group consisting of: SEQ ID NO: 17; a peptide comprising 9, 10, 11, 12, 13, or 14 consecutive amino acid residues of SEQ ID NO: 17; SEQ ID NO: 51; and their pharmaceutically acceptable salts, wherein said fragment is characterized by a capacity to bind to TGF-β1. In a more preferred embodiment, said peptide is a peptide whose amino acid sequence is SEQ ID NO: 17, or a pharmaceutically acceptable salt thereof. In another preferred embodiment, said peptide is a peptide whose amino acid sequence comprises 9, 10, 11, 12, 13, or 14 consecutive amino acid residues of SEQ ID NO:17, or their pharmaceutically acceptable salts, wherein said peptide has the capacity to bind to TGF-β1, such as a peptide selected from the group formed by the peptides identified by SEQ ID NO: 17, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, preferably a peptide whose amino acid sequence is SEQ ID NO: 33 or SEQ ID NO: 34. In another particular embodiment, said peptide is a peptide whose amino acid sequence is SEQ ID NO: 51. In a preferred embodiment said peptide is a peptide whose amino acid sequence is SEQ ID NO: 17 or SEQ ID NO: 51.

In a particular embodiment, the peptide capable of binding to TGF-β1 and inhibiting its biological activity of TGF-β1, or a pharmaceutically acceptable salt thereof, is administered, for treating corneal fibrosis, in the form of a topical pharmaceutical composition suitable for ophthalmic application, such as eyedrops, ointments, creams, etc.; in a preferred embodiment, the peptide capable of binding to TGF-β1 and inhibiting its biological activity of TGF-β1, or a pharmaceutically acceptable salt thereof, is administered, for treating corneal fibrosis, in the form of a topical pharmaceutical composition suitable for ophthalmic application further comprising hyaluronic acid or a pharmaceutically acceptable salt thereof, such as sodium hyaluronate, suitable for ophthalmic administration, e.g., in the form of eyedrops, ointments or the like.

In another aspect, the invention relates to a method of treating corneal haze which comprises administering to a subject in need of treatment a therapeutically effective amount of a peptide capable of binding to TGF-β1 and inhibiting the biological activity of TGF-β1, or a pharmaceutically acceptable salt thereof. In a particular embodiment, said peptide is a peptide whose amino acid sequence comprises SEQ ID NO: 51, a peptide capable to bind to TGF-β1 and inhibit its biological activity, or a pharmaceutically acceptable salt thereof. In another particular embodiment, said peptide comprises 9, 10, 11, 12, 13, 14 or 15 consecutive amino acid residues of a sequence of amino acids selected from SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22. In another particular embodiment, said peptide is a peptide comprising 9, 10, 11, 12, 13, 14 or 15 consecutive amino acid residues of a sequence of amino acids selected from SEQ ID NO: 3, SEQ ID NO: 4, SEQ ID NO: 6, SEQ ID NO: 11, SEQ ID NO: 13, SEQ ID NO: 14, SEQ ID NO: 17 and SEQ ID NO: 18, or a pharmaceutically acceptable salt thereof. In a preferred embodiment, said peptide is a peptide selected from the group consisting of: SEQ ID NO: 17; a peptide comprising 9, 10, 11, 12, 13, or 14 consecutive amino acid residues of SEQ ID NO: 17; SEQ ID NO: 51; and their pharmaceutically acceptable salts, wherein said fragment is characterized by a capacity to bind to TGF-β1. In a more preferred embodiment, said peptide is a peptide whose amino acid sequence is SEQ ID NO: 17, or a pharmaceutically acceptable salt thereof. In another preferred embodiment, said peptide is a peptide whose amino acid sequence comprises 9, 10, 11, 12, 13, or 14 consecutive amino acid residues of SEQ ID NO:17, or their pharmaceutically acceptable salts, wherein said peptide has the capacity to bind to TGF-β1, such as a peptide selected from the group formed by the peptides identified by SEQ ID NO: 17, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, preferably a peptide whose amino acid sequence is SEQ ID NO: 33 or SEQ ID NO: 34. In another particular embodiment, said peptide is a peptide whose amino acid sequence is SEQ ID NO: 51. In a preferred embodiment said peptide is a peptide whose amino acid sequence is SEQ ID NO: 17 or SEQ ID NO: 51.

In a particular embodiment, the peptide capable of binding to TGF-β1 and inhibiting its biological activity of TGF-β1, or a pharmaceutically acceptable salt thereof, is administered, for treating corneal haze, in the form of a topical pharmaceutical composition suitable for ophthalmic application, such as eyedrops, ointments, creams, etc.; in a preferred embodiment, the peptide capable of binding to TGF-β1 and inhibiting its biological activity of TGF-β1, or a pharmaceutically acceptable salt thereof, is administered, for treating corneal haze, in the form of a topical pharmaceutical composition suitable for ophthalmic application further comprising hyaluronic acid or a pharmaceutically acceptable salt thereof, such as sodium hyaluronate, suitable for ophthalmic administration, e.g., in the form of eyedrops, ointments or the like.

The peptides of the invention, as well as P144 (SEQ ID NO: 51), can be obtained by conventional methods, such as for example by solid phase chemical synthesis, purified with high performance liquid chromatography (HPLC), and, if desired, analyzed by conventional techniques such as for example sequencing and mass spectrometry, amino acid analysis, nuclear magnetic resonance techniques, etc.

Alternatively, the peptides of the invention can be obtained by recombinant DNA technology. Thus, in another aspect, the invention yields a DNA sequence encoding a peptide of the invention. Said DNA sequence can easily be deduced from the amino acid sequence of the peptide.

Said DNA sequence can be contained within a DNA construct. Thus, the invention yields a DNA construct comprising a sequence of DNA that encodes a peptide of the invention. This DNA construct can operatively incorporate a regulatory sequence for the expression of the DNA sequence encoding the peptide of the invention. Control sequences are sequences that control and regulate the transcription and, where applicable, the translation of the peptide of the invention; they include promoter and terminator sequences, etc., which are functional in transformed host cells, that comprise the mentioned DNA sequence or DNA construct. In a particular embodiment, said control expression sequence is functional in bacteria. Advantageously, this DNA construct also comprises a marker or gene that encodes a motif or phenotype which allows selection of the transformed host cell by means of the DNA construct. The DNA construct provided by this invention can be obtained by means of methods which are well known in the state of the art [Sambrook et al., "Molecular cloning, a Laboratory Manual", $2^{nd}$ ed., Cold Spring Harbor Laboratory Press, N.Y., 1989 Vol. 1-3].

The DNA sequence or DNA construct provided by this invention can be inserted in an appropriate vector. Thus, in another aspect, the invention relates to a vector, such as an expression vector, that comprises the mentioned DNA sequence or DNA construct. The choice of vector will depend on the host cell into which it is to be inserted subsequently. As an example, the vector into which the DNA sequence is inserted can be a plasmid or vector which, upon insertion into the cell, may or may not integrate to the cell genome. The vector can be obtained by conventional methods known by the skilled person [Sambrok et al., 1989, cited supra].

In another aspect, the invention relates to a host cell, such as a transformed host cell, that comprises a DNA sequence or DNA construct provided by this invention.

In another aspect, the invention relates to a process for producing a peptide of the invention which comprises growing a host cell with the DNA sequence or DNA construct provided by the invention, under conditions that allow the production of the mentioned peptide of the invention, and, if desired, recovering the peptide of the invention. The conditions for optimizing culture of the host cell will depend on the type of host cell employed. If desired, the process for producing the peptide of the invention includes isolation and purification of the peptide.

In another aspect, the invention relates to the use of these DNA sequences and DNA constructs in the manufacture of vectors and cells for the treatment by gene therapy of diseases and pathological alterations associated with excessive or deregulated TGF-β1 expression. In accordance with this aspect of the invention, these DNA sequences or DNA constructs are placed in contact with a genetic transfer vector (e.g., a viral or non-viral vector). Appropriate viral vectors for carrying out this aspect of the invention include but are not limited to the following vectors: adenoviral, adenoassociated, retroviral, lentiviral, alphaviral, herpesviral, coronavirus derived vectors, etc. Appropriate non-viral vectors for carrying out this aspect of the invention include but are not limited to naked DNA, liposomes, polyamines, dendrimers, cationic glycopolymers, liposome-polycation complexes, proteins, receptor-mediated genetic transfer systems, etc.

The following examples illustrate the invention and should not be taken to reflect limitations to the latter.

EXAMPLE 1

Figure 1:
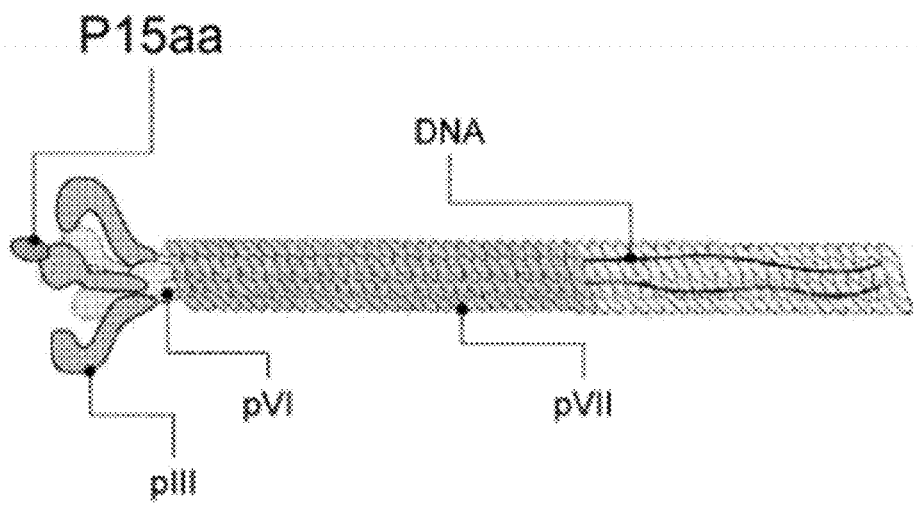
FIG. 1 schematically shows the position of a 15-amino acid (aa) peptide, genetically fused to protein pIII, on the surface of filamentous bacteriophage M13.
Figure 2:
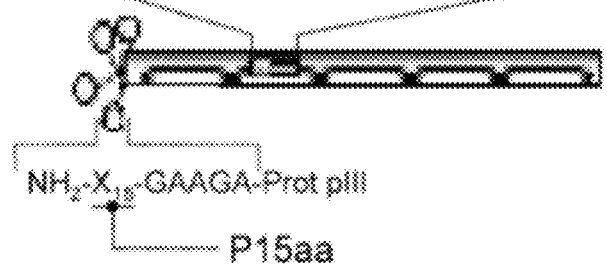
FIG. 2 schematically shows the genetic position of the insert, which encodes a 15-aa peptide, in the genome of bacteriophage M13 and the position of the peptide in the sequence of protein pIII.

Selection of Peptides that Bind to TGF-β1 Using a Phage-Displayed Peptide Library In order to obtain sequences of 15 amino acids capable of high affinity binding to TGF-β1, and offering a possible inhibitory activity upon the biological activity of this cytokine, use was made of an in vitro selection technique based on technology developed from phage-displayed peptide libraries. These libraries comprise a plurality of filamentous bacteriophages (M13), each one containing a peptide genetically fused to a protein of the virus envelope—in this case bound to the N-terminal end of envelope protein pIII (FIG. 1). In this way the phage displays a 15-aa peptide at the surface of each one of the 5 copies of the surface protein pIII, whereas the DNA sequence encoding the peptide is contained within the phage. In the phage libraries, the sequence encoding the peptide originates from a sequence degenerated in each one of the 15 positions with the 20 natural amino acids, thus allowing the presentation of $1.1 \times 10^{12}$ possible sequences of 15 amino acids in different phages. The physical ratio, 1:1, between the peptide sequence and the DNA encoding it within the bacteriophage allows the selection (from a broad range of variants) of those sequences that specifically bind to TGF-β1. This process is carried out via an in vitro selection protocol known as "biopanning".

The phage-displayed library used for this example originates from a second amplification of the primary library described by T. Nishi, H. Tsuri and H. Saya [Exp. Med. (Japan) 11, 1759 (1993)], and supplied by the laboratory of George P. Smith.

Selection Technique Biopanning

Figure 3:
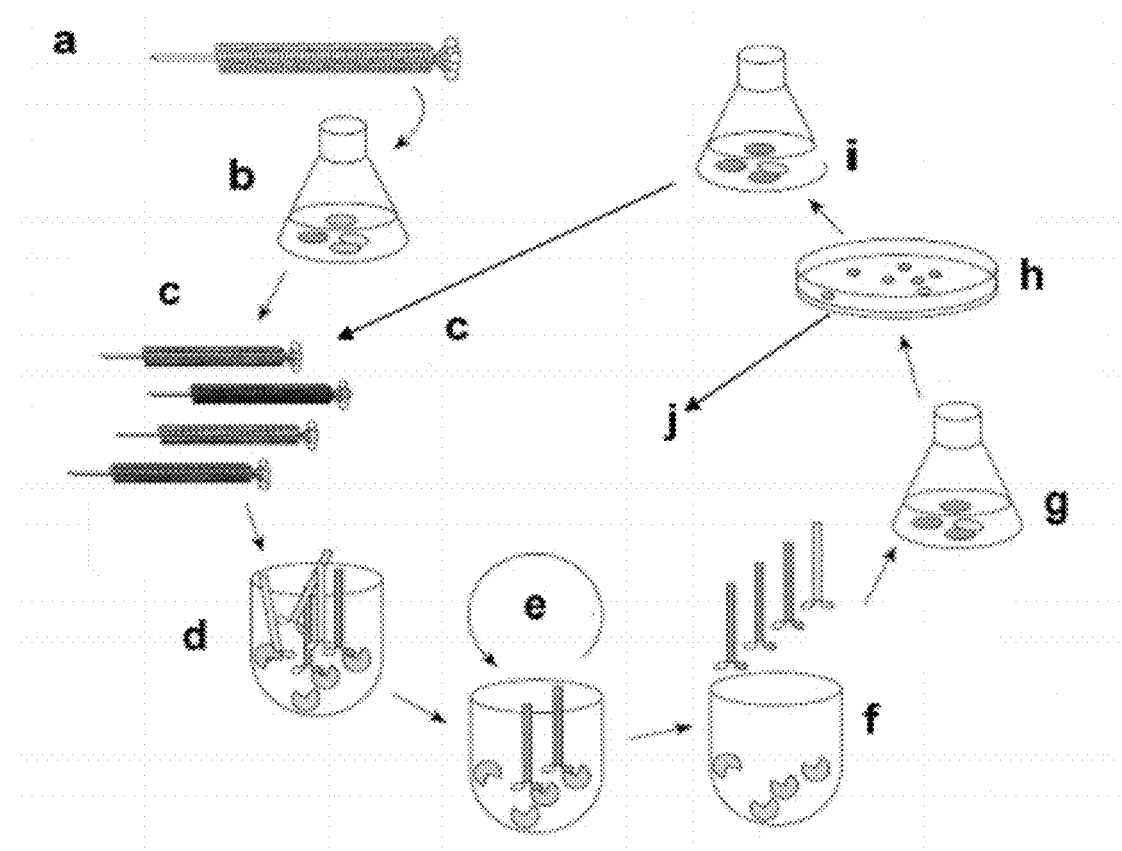
FIG. 3 schematically shows the selection of peptides based on the "biopanning" technique. The biotinylated TGF-β1 is immobilized on plates containing streptavidin (through biotin-streptavidin bonding). Phages from the library are selected on the basis of the interaction between TGF-β1 and the peptides presented by the phages. The phages with low affinity for TGF-β1 are eliminated by washings. The phages retained in the plate are eluted by lowering the pH. After three cycles of enrichment of phages with high affinity for TGF-β1, the phages are isolated and sequenced (see Example 1) [Legends to FIG. 3: "a": Library of phages presenting 15-aa peptides; "b": Infection in E. coli (K91Kan) (amplification); "c": Purification of the phages; "d": Incubation of the phages with decreasing concentrations of TGF-β1; "e": Washings; "f": Elution of the bound phages (↓pH); "g": Infection in strain of E. coli; "h": Selection of infected colonies (tetracycline); "i": Amplification of the selected phages; and "j": Sequencing of DNA (corresponding to the peptide) after three "biopanning" cycles].

This technique involves incubating a set of phages representative (to practical effects) of all the 15-aa variants, in a plate blocked with streptavidin (10 μg/ml in 0.1 M NaHCO$_3$, during 2 h at room temperature) to which biotinylated TGF-β1 is added. The biotinylated TGF-β1 is anchored to the plate through the biotin-streptavidin interaction, thereby it remains correctly displayed for its interaction with the peptides carried by the phages. TGF-β1 contacts the peptides carried by the phages at a concentration of $3 \times 10^4$ virus/ml. After about 12 hours incubation, unbound phages are eliminated by 5 washings with PBS/Tween (phosphate buffered saline/polyoxyalkylene derivatives of sorbitan fatty acid esters). Bound phages are then eluted by lowering the pH (elution buffer) which breaks the interactions between TGF-β1 and the peptides displayed by the phages. The eluted phages are then amplified by infection in a bacterial strain (E. coli). The process is repeated three cycles so that an enrichment in the content of phages which specifically bind, and with high affinity, to TGF-β1 is achieved (FIG. 3). The concentration of biotinylated TGF-β1 used to block the plates is gradually reduced in each cycle, e.g., from 2.5 to 0.01 μg/ml, and finally to 0.001 μg/ml. Thus, the phages selected in each cycle show more and more affinity for TGF-β1. At the end of the process, phages which have been selected for their affinity for TGF-β1, are sequenced by using primers, after isolation by tetracycline resistance of the genetically modified phages after infecting E. coli cells. This allows obtaining the peptides sequences displayed in the phages of a number of clones obtained from isolated colonies. The number of times which a sequence is repeated, corresponding to a 15 amino acids peptide carried by each clone, from the total of sequenced colonies is an indication of the degree of relative affinity of said 15 amino acids sequence for TGF-β1.

Sequence of Peptides

The selection of clones, obtained from the "biopanning", was carried out by selection of the bacterial colonies infected with the phages in the presence of a bacterial antibiotic; the bacteria resistance is acquired by a tetracycline resistance gene encoded by the phage genome. Thus, only those colonies infected with bacteriophages are able to grow. This means that each colony contains the genome of only one phage coding for only one peptide presented in its surface.

A total number of 108 colonies of phage-infected bacteria were obtained from the last selection cycle of "biopanning". The sequence of the regions coding for the peptides present in the pIII protein was carried out using primers identified with SEQ ID NO: 23. This afforded different peptide sequences as shown in Table 1. This table also reflects the number of colonies (clones) carrying said sequences.

TABLE 1

Amino acid sequences from phages that bind to TGF-β1

| SEQ ID NO: | No. colonies |
| --- | --- |
| 1 | 6 |
| 2 | 1 |
| 3 | 41 |
| 4 | 18 |
| 5 | 1 |
| 6 | 12 |
| 7 | 2 |
| 8 | 2 |
| 9 | 1 |
| 10 | 1 |
| 11 | 4 |
| 12 | 1 |
| 13 | 6 |
| 14 | 2 |
| 15 | 1 |
| 16 | 1 |
| 17 | 3 |
| 18 | 1 |
| 19 | 1 |
| 20 | 1 |
| 21 | 1 |
| 22 | 1 |

The number of clones (colonies) of each sequence gives an approximate indication of the degree of affinity of the peptide for TGF-β1, that is, the more colonies the more binding affinity. However, the degree of affinity does not correlate to the capacity of the peptide to block the biological activity of TGF-β1. Indeed, the most active peptide, identified by SEQ ID NO: 17 (see Tables 2 and 3), is represented by 3 clones, while the peptide identified by SEQ ID NO: 3, which is represented by 41 clones, is much less active in the acute liver damage assay (Table 3). While not being adhered to any concrete theory, this observation might be explained by postulating that the most active peptide probably blocks the binding of TGF-β1 to its receptor.

Comparison of the Peptide Sequences

Figure 4:
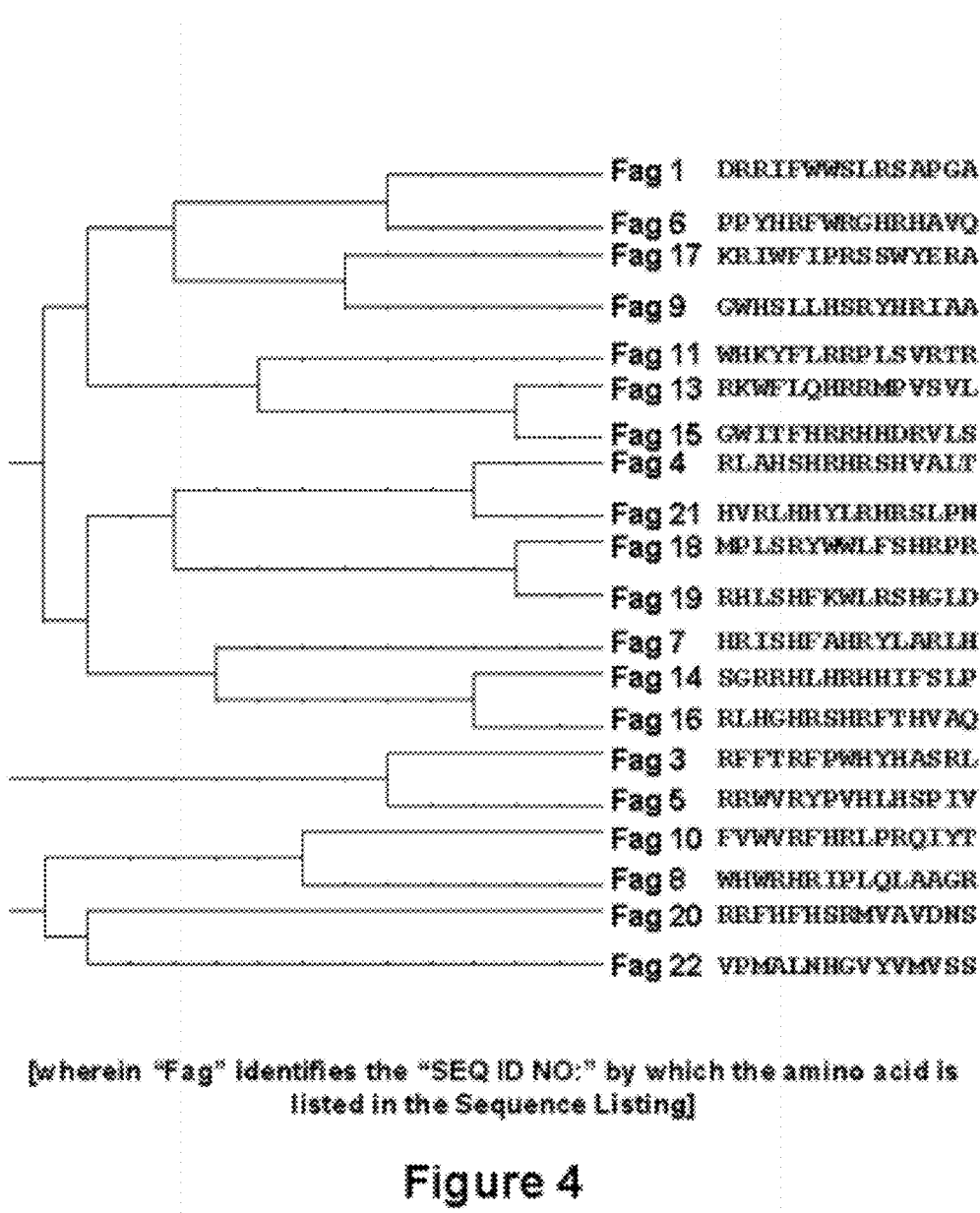
FIG. 4 provides a representation of a sequence analogy tree among the 15-aa peptides identified by means of a phage-displayed peptide library.

The sequences obtained were analyzed using the CLUSTAL W program (1.81). This program generates multiple sequences grouping based on the amino acid sequence analogies. Peptides are consequently grouped in different structural families based on sequence analogies of the peptides (FIG. 4). Based on these analogies, lesser TGF-β1 bonding motifs or groups of peptides that bind to different TGF-β1 regions can be suggested.

EXAMPLE 2

Figure 5:
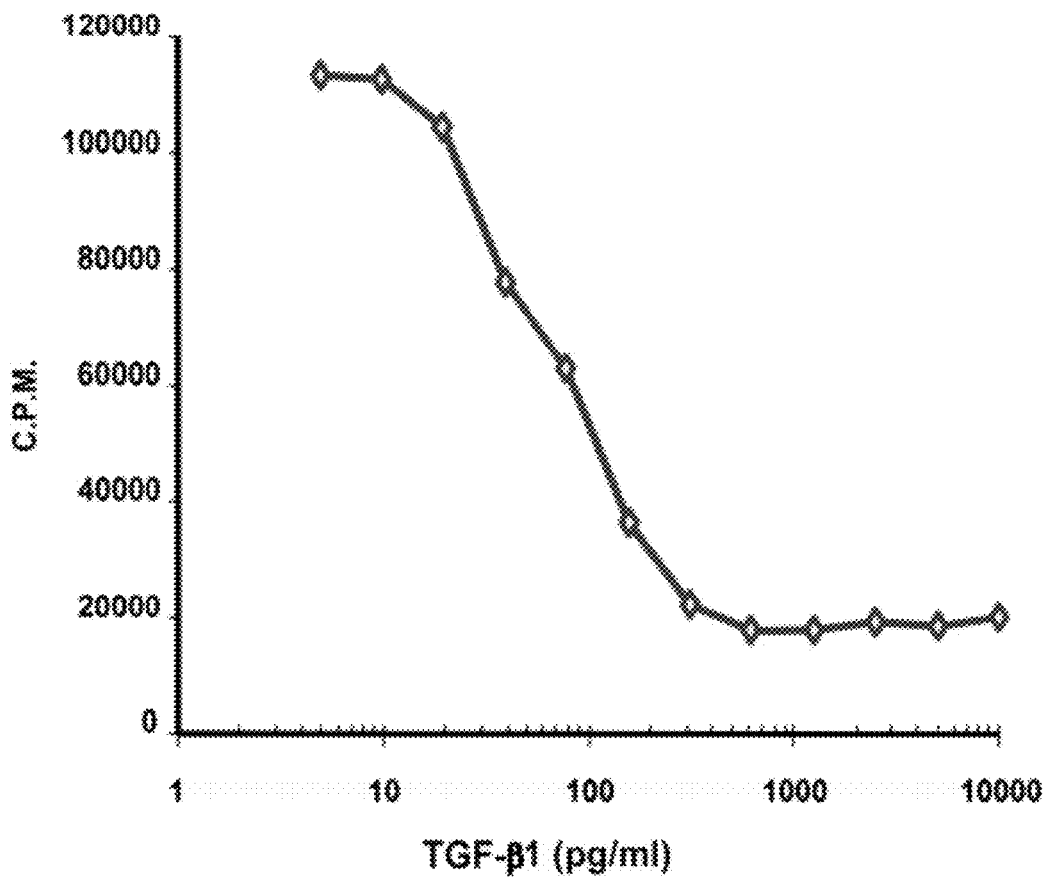
FIG. 5 provides a diagrammatic representation of the effect of TGF-β1 concentration on growth of the Mv-1-Lu cell line, expressed as the uptake of tritiated thymidine in counts per minute (c.p.m.).

Inhibition of In Vitro TGF-β1 Biological Activity by Using Peptides in Mv-1-Lu Cell Proliferation Assays The cell line Mv-1-Lu (CCL-64, American Type Cell Culture, Virginia, USA) derives from mink pulmonary epithelium, grows as a monolayer, and responds to the presence of TGF-β1 by decreasing its proliferation (FIG. 5). Thus, the peptide-mediated inhibition of this cytokine is able to restore cell growth and reflects the capacity of the different peptides to inhibit the biological activity of TGF-β1 in vitro. The peptides tested were obtained by peptide synthesis, in accordance to conventional procedures (Merrifield R B. J Am Chem Soc 1963; 85:2149-2154; Atherton E et al. J Chem Soc Perkin Trans 1981; 1:538-546).

The Mv-1-Lu cells are cultured to confluence in complete medium [RPMI-1640 supplemented with L-glutamine, sodium pyruvate, antibiotics and 10% fetal bovine serum (FBS)] at 37° C. and in 5% $CO_2$ in 162 $cm^2$ bottles (Costar Corporation, CA, USA). Following trypsinization, the cells are cultured in 200 µl of complete medium in 96-well plates at an initial density of 5,000 cells/well at 37° C. and in 5% $CO_2$ during 6 hours to ensure adhesion. Then, different concentrations of the peptides to be tested are added, starting from 200 µg/ml, and following 200 pg/ml of TGF-β1 (Roche) are added. After 12 hours of incubation 1 µCi of methyl-3H-thymidine (Amersham Life Science, Buckinghamshire, United Kingdom) is added per well in 25 µl of clean medium (RPMI-1640). The plate is incubated for 12 more hours under the same conditions. Finally, the cells are harvested (Filtermate 196 Harvester, Packard), transferring the tritiated thymidine, incorporated in the course of DNA synthesis, to plates (UniFilter-96 GF/C®, Perkin Elmer). Following the addition of scintillation fluid, the radioactivity was quantified using a scintillation counter (Top Count, Microplate Scintillation Counter, Packard). As positive and negative control, use was made of the incorporation of tritiated thymidine in the absence and presence of TGF-β1, respectively. The inhibition of TGF-β1 activity in this test was calculated based on the following formula:

$$\% \text{ Inhibition} = \frac{100 \times (\text{cpm with peptide} - \text{cpm negative control})}{(\text{cpm positive control} - \text{cpm negative control})}$$

The negative control represents the incorporation of tritiated thymidine in the presence of TGF-β1 but in the absence of peptide, whereas the positive control refers to the incorporation of tritiated thymidine in the absence of TGF-β1 and peptide. Thus, according to the capacity of the peptides to revert the cytokine repressor effect on Mv-1-Lu cell line proliferation, percentage of TGF-β1 biological activity inhibition by the peptides can be measured (Table 2).

TABLE 2

Effect of the peptides obtained by selection by "biopanning" on the inhibition of in vitro TGF-β1 biological activity, as calculated from a Mv-1-Lu cell line growth reestablishment assay

| SEQ ID NO: | % Inhibition |
|---|---|
| 1 | 3.33 ± 4.3 |
| 2 | −0.96 ± 0.83 |
| 3 | 25.39 ± 1.7 |
| 4 | 5.53 ± 7.2 |
| 5 | 15.78 ± 7.7 |
| 6 | 12.85 ± 4.5 |
| 7 | −24.96 ± 0.75 |
| 8 | 15.67 ± 8.5 |
| 9 | 4.98 ± 9.5 |
| 10 | −4.58 ± 0.9 |
| 11 | 27.36 ± 0.9 |
| 12 | 10.70 ± 0.9 |
| 13 | 17.97 ± 4.3 |

TABLE 2-continued

Effect of the peptides obtained by selection by "biopanning" on the inhibition of in vitro TGF-β1 biological activity, as calculated from a Mv-1-Lu cell line growth reestablishment assay

| SEQ ID NO: | % Inhibition |
|---|---|
| 14 | 3.62 ± 5.6 |
| 15 | 13.45 ± 9.5 |
| 16 | 9.47 ± 4.2 |
| 17 | 38.92 ± 2.3 |
| 18 | 21.29 ± 2.8 |
| 19 | 9.71 ± 3.2 |
| 20 | 6.16 ± 9.5 |
| 21 | 13.40 ± 3.2 |
| 22 | 4.13 ± 1.4 |
| P144 | 7.26 ± 3.53 |

The peptides identified as SEQ ID NO: 3, 11, 17 and 18 inhibit the biological activity of TGF-β1 in vitro with a percentage of inhibition higher than 20%.

Additionally, in order to assess the capacity of the peptides to revert the suppressor effect of TGF-β1 on Mv-1-Lu cell line proliferation as previously described, the activity of the peptide identified as P144 in the Spanish patent application ES 2146552 A1 was compared with the activity of the peptide identified as SEQ ID NO: 17. The peptide identified as SEQ ID NO: 17 exhibited an improved capacity.

EXAMPLE 3

Figure 6:
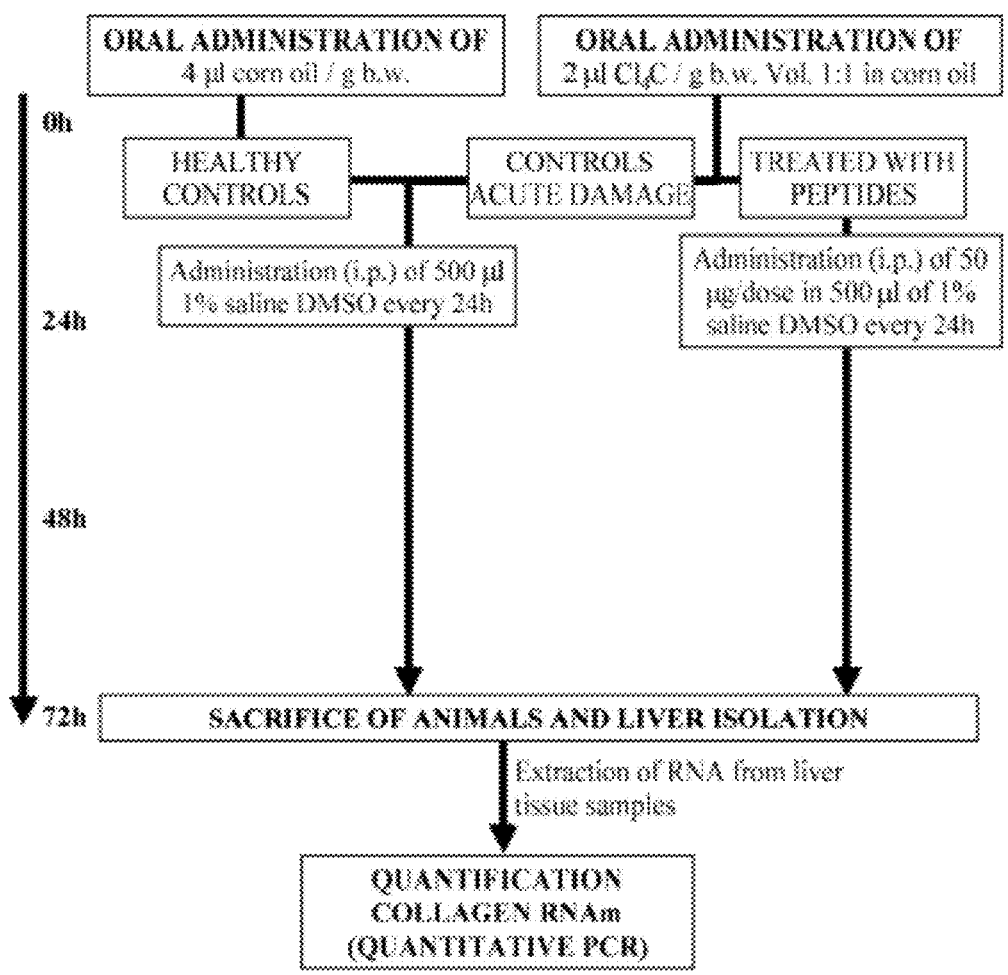
FIG. 6 provides a diagrammatic representation of the acute liver damage induction protocol (see Example 3).

In Vivo Inhibition of TGF-β1 Biological Activity by Peptides Using a Model of Acute Liver Damage Induced by $CCl_4$ Acute liver damage generates a cascade of effects and physiological responses, including elevations in the concentrations of TGF-β1. This elevation is responsible for the expression of the type I collagen gene, among others. In this model of acute liver damage, female Balb/C mice weighing 25 to 30 g, were orally administered a dose of 2 µl of $CCl_4$ (per gram of body weight) dissolved in an equivalent volume of corn oil (volumetric ratio of 1:1). The control group received an equivalent volume of corn oil only, and the treated groups received (following the single oral administration of $CCl_4$ in corn oil) 50 µg of peptide in 500 µl of 1% physiological saline solution in DMSO (dimethyl sulfoxide) every 24 h. After 72 hours all animals were sacrificed, and the liver samples were processed. To evaluate mRNA expression, liver tissue was frozen in liquid nitrogen and stored at −80° C. until further use. Other liver tissue samples were stored in OCT® or Tissue-Tek® (Sakura Finetek B.V.) and processed in the same way as the samples used for mRNA studies. Other liver samples were fixed in 10% buffered formalin solution, embedded in paraffin and processed for their histological evaluation. The amount of mRNA encoding type I collagen was quantified in all groups using a quantitative polymerase chain reaction (PCR) technique. FIG. 6 shows a flow chart of the induction, obtaining of the samples and results quantification in the acute liver damage assay. The capacity of the testing peptides to block the acute damage, as assessed by measuring the levels of induced type I collagen mRNA was quantified by real time PCR. Table 3 shows the degree of inhibition of the expression of collagen type I mRNA by phage-derived peptides. The peptides tested were obtained by conventional solid peptide synthesis procedures (Merrifield R B. J Am Chem Soc 1963; 85:2149-2154; Atherton E et al. J Chem Soc Perkin Trans 1981; 1:538-546).

TABLE 3

Effect of the peptides obtained by selection by "biopanning" on the inhibition of in vivo TGF-β1 biological activity, as calculated on the basis of the inhibition of type I collagen mRNA induction in a model of acute liver damage

| SEQ ID NO: | % Inhibition |
|---|---|
| 1 | 0.69 |
| 2 | 36.6 ± 30.7 |
| 3 | 2.09 |
| 4 | 51.30 ± 15.3 |
| 5 | Neg |
| 6 | 74.94 ± 25.3 |
| 7 | Neg |
| 8 | Neg |
| 9 | 26.59 |
| 10 | Neg |
| 11 | 39.34 ± 21.9 |
| 12 | Neg |
| 13 | 32.70 |
| 14 | 49.84 ± 24 |
| 15 | 14.26 |
| 16 | Neg |
| 17 | 93.09 ± 9.6 |
| 18 | Neg |
| 19 | 12.12 |
| 20 | 1.41 |
| 21 | Neg |
| 22 | Neg |
| P144 | −3.51 ± 36 |

(Neg: negative)

The peptides identified as SEQ ID NO: 2, 4, 6, 11, 14 and 17 inhibit the biological activity of TGF-β1 in vivo, with a percentage of inhibition greater than 35%.

Additionally, in order to assess the capacity of the peptides to inhibit type I collagen mRNA induction in a model of acute liver damage in mice as previously described, the activity of the peptide identified as P144 in the Spanish patent application ES 2146552 A1 was compared with the activity of the peptide identified as SEQ ID NO: 17. In this comparative assay, it was observed that the peptide identified as SEQ ID NO: 17 inhibits the expression of type I collagen mRNA to a much greater extent than the peptide identified as P144 in the Spanish patent application ES 2146552 A1, which does not show any activity in this assay. The results obtained by the comparative tests (Examples 2 and 3) show that a peptide representative of the peptides of this invention (the peptide identified as SEQ ID NO: 17) is more active than a peptide representative of Spanish patent application ES 2146552 A1 (the peptide identified as P144) in the proliferation tests with Mv-1-Lu cells and in a model of acute liver damage.

EXAMPLE 4

In Vitro Inhibition of TGF-β1 Biological Activity by Truncated Peptides from the Peptide of SEQ ID NO: 17 in a Proliferation Assay with Mv-1-Lu Cells This example shows the inhibitory activity of some peptides whose amino acid sequences comprise between 3 and 15 consecutive amino acid residues of one of the amino acid sequences of the invention.

Comparisons have been made of the activity of truncated peptides (derived from peptide sequence SEQ ID NO: 17) versus the complete sequence, in terms of the capacity to revert the suppressor effect of TGF-β1 upon proliferation of the Mv-1-Lu cell line. To this effect, and to determine the minimum sequence of peptide SEQ ID NO: 17 capable of inhibiting the biological activity of TGF-β1 in vitro, truncated versions of this peptide were synthesized, with truncation at the N-terminal end, C-terminal end or in both ends of the molecule. The peptides tested were obtained by peptide synthesis following conventional procedures (Merrifield R B. J Am Chem Soc 1963; 85:2149-2154; Atherton E et al. J Chem Soc Perkin Trans 1981; 1:538-546). Following the same methodology described in Example 2, the activity of truncated peptides versus the complete sequence of the peptide SEQ ID NO: 17 was quantified, in terms of a proliferation assay of the Mv-1-Lu cell line.

TABLE 4

Effect of the truncated peptides obtained from the peptide SEQ ID NO: 17 on the inhibition of in vitro TGF-β1 biological activity, as calculated from a Mv-1-Lu cell line growth reestablishment assay

| SEQ ID NO: | Sequence of peptide | % Inhibition |
|---|---|---|
| 17 | KRIWFIPRSSWYERA | 28.5 ± 3.9 |
| 24 (T1) | RIWFIPRSSWYERA | 9.4 ± 0.4 |
| 25 (T2) | RIWFIPRSSWYER | 6.2 ± 1.5 |
| 26 (T3) | IWFIPRSSWYERA | 4.5 ± 1.8 |
| 27 (T4) | IWFIPRSSWYE | 1.4 ± 2.5 |
| 28 (T5) | WFIPRSSWY | 3.1 ± 0.9 |
| 29 (T6) | WFIPRSSWYERA | 2.7 ± 1.8 |
| 30 (T7) | FIPRSSWYERA | −0.3 ± 3.0 |
| 31 (T8) | IPRSSWYERA | 3.4 ± 1.4 |
| 32 (T9) | PRSSWYERA | 3.8 ± 1.6 |
| 33 (T10) | KRIWFIPRSSWYER | 31.4 ± 7.0 |
| 34 (T11) | KRIWFIPRSSWY | 34.4 ± 7.9 |
| 35 (T12) | KRIWFIPRSS | 6.0 ± 0.4 |
| 36 (T13) | KRIWFIPRS | 6.2 ± 2.5 |

As shown in Table 4, in this comparative assay, the removal of lysine (K) from the N-terminal end implies a loss of activity of peptide SEQ ID NO: 17 from 28.5% to 9.4%. In contrast, the removal of up to three amino acids from the C-terminal end does not affect the activity of the peptide. Also, removal of the aromatic amino acids tyrosine (Y) and tryptophan (W), abrogates the activity of the peptide. This allows reducing the original peptide SEQ ID NO: 17 to a 12 amino acid sequence (KRIWFIPRSSWY) [SEQ ID NO: 34] not affecting its TGF-β1 in vitro inhibitory activity.

EXAMPLE 5

Therapeutic Effect of a Peptide Inhibitor of TGF-β1 on Pulmonary Fibrosis

The effects of the peptide whose amino acid sequence is SEQ ID NO: 17 (hereinafter referred to as "P17") on the differentiation of fibroblasts (IMR-90 lung fibroblast) into myofibroblasts in vitro, and on the development of bleomycin-induced pulmonary fibrosis in mice, are investigated in this Example.

5.1 Materials and Methods

5.1.1 Materials

TGF-β1 inhibitor peptide P17 (SEQ ID NO: 17), as well as control peptide P301, encompassing amino acids 301-315 of HIV-1 gp120, which is unable to bind to TGF-β1, were purchased from NeoMPS, Inc. (Strasbourg, France). Peptide purity was at least 98% per high-performance liquid chromatography (HPLC) and mass spectrometry (MS). Recombinant human TGF-β1 was purchased from R&D Systems (Minneapolis, Minn.).

5.1.2 Human Lung Fibroblast Culture

IMR-90 human lung fibroblasts (ATCC, Manassas, Va.) were cultured in EMEM medium (Cambrex, Belgium) supplemented with 10% fetal bovine serum (FBS), 1 mM sodium pyruvate, 0.1 mM nonessential amino acids, 100 U/ml penicillin and 100 µg/ml streptomycin (Gibco BRL, UK). For experiments, $6\times10^4$ cells/well were cultured in 6-well plates in 2 ml of medium and when they were 80% confluent, medium was replaced with serum-free EMEM for 48 h to induce quiescence. TGF-β1 (5 ng/ml) and P17 (100 µg/ml) were co-incubated for 90 min at 37° C. to allow binding of both molecules before addition to cell cultures. Quiescent cells were then stimulated with TGF-β1 and/or P17 for up to 6 or 24 h. After these incubation periods, fibroblasts were harvested for gene and protein analysis, respectively.

5.1.3 Model of Bleomycin-Induced Pulmonary Fibrosis

Female C57BL/6 mice (6-8 weeks of age) were obtained from Harlan SL (Barcelona, Spain) and maintained in accordance with the ethical committee of Universidad de Navarra (Spain) for the experimental use of animals. Lung injury was induced with 0.08 units/mouse of bleomycin sulfate (Sigma, Spain) diluted in 200 µl of phosphate buffered saline (PBS). Briefly, the suspension of bleomycin was instilled by pippeting into the nose of mice previously anesthetized with 2% isoflurane vapor. PBS was instilled in mice as a negative control for pulmonary fibrosis (PF), following the same procedures. Peptide treatment was started two days after bleomycin challenge and it was administered intraperitoneally in 500 µl of PBS on alternate days. Mice received high (75 µg/mouse) or low (25 µg/mouse) doses of P17, or the high dose (75 µg/mouse) of control peptide P301. Lungs were obtained 15 or 26 days after bleomycin administration to evaluate profibrogenic gene expression or histological damage, respectively. To study the therapeutic effect of P17 in the development of fibrosis, it was administered daily ten days after bleomycin challenge, once fibrosis was established. Twenty six days after bleomycin instillation, mice were sacrificed and lung samples were fixed in order to evaluate histological damage.

5.1.4 Real Time PCR Analysis in IMR-90 Fibroblasts and Lung Tissue

Total RNA was purified from IMR-90 fibroblasts and whole lung samples using Ultraspec RNA (Biotecx; Houston, Tex.) according to the manufacturer's instructions. First, 1 µg of RNA was incubated with Dnase I (2 U/µl) (Gibco-BRL) for 30 min at 37° C. Then, samples were reverse-transcribed with the M-MLV Reverse transcriptase (Gibco-BRL) in the presence of RNaseOUT (Gibco-BRL) with ramdon hexamers and poly (dT) oligos according to the manufacturer's protocol. Expression of human Connective Tissue Growth Factor (CTGF) mRNA induced by TGF-β1 in IMR-90 fibroblasts was measured by real time RT-PCR using an ICycler and IQ SYBR Supermix (Bio-Rad, Italy). Actin was used as endogenous reference housekeeping gene. For in vivo analysis, expression of murine Fibronectin (FN), extra domain A of Fibronectin (EDA-FN), Collagen type I and Interferon gamma (IFN-γ) was measured in lungs, using Histone 3 as internal control. Primers designed are listed in Table 5. The amount of each transcript was expressed by the formula:

$$2^{\Delta Ct} \; (\Delta Ct = Ct(\text{control gene}) - Ct(\text{gene})),$$

wherein Ct is the threshold cycle number at which an increase in the signal associated with exponential growth of PCR products begins to be detected using Bio-Rad analysis software.

TABLE 5

| Primer sequences used for real time RT-PCR | | |
|---|---|---|
| Gene | Sense primer (5'-3') | Antisense primer (5'-3') |
| muCollagen Type I | TTTGGAGAGAGCATGACCGA (SEQ ID NO: 37) | TGCTGTAGGTGAAGCGACTGTT (SEQ ID NO: 38) |
| muFN | CTATCTATGCTGTGGAGGAG (SEQ ID NO: 39) | GAGTTTGGTGGTCTGTTGTG (SEQ ID NO: 40) |
| muEDA-FN | ACATTGATCGCCCTAAAGGAACT (SEQ ID NO: 41) | TGTGGACTGGATTCCAATCAGGGG (SEQ ID NO: 42) |
| MuIFNγ | TCAAGTGGCATAGATGTGGAAGAA (SEQ ID NO: 43) | TGGCTCTGCAGGATTTTCATG (SEQ ID NO: 44) |
| muHistone 3 | AAAGCCGCTCGCAAGAGTGCG (SEQ ID NO: 45) | CTCCTGCAAAGCAC (SEQ ID NO: 46) |
| HuCTGF | TGATTAGAGCCAACTGCCTG (SEQ ID NO: 47) | GGTATGTCTTCATGCTGGTG (SEQ ID NO: 48) |
| HuActin | AGCCTCGCCTTTGCCGA (SEQ ID NO: 49) | CTGGTGCCTGGGGCG (SEQ ID NO: 50) | mu: murine; hu: human.

5.1.5 Western Blot Analysis in IMR-90 Cells

To assess alpha-Smooth Muscle Actin (αSMA) expression, IMR-90 fibroblasts were lysed with RIPA buffer containing 10 U/ml leupeptin, 10 U/ml pepstatin, 1 mM phenylmethanesulfonylfluoride (PMSF), 1 mM $Na_3VO_4$ and 1 mM NaF. Then, equal amounts of protein were electrophoresed through 10% SDS polyacrylamide gels and transferred onto nitrocellulose membranes. Membranes were analyzed for expression of αSMA protein using anti-αSMA monoclonal antibody (Sigma-Aldrich) at a dilution of 1:2000 and horseradish peroxidase-labeled anti-mouse IgG (Sigma-Aldrich). Expression of actin was detected using anti-actin monoclonal antibody (Sigma-Aldrich) (1:2000 dilution) and horseradish peroxidase-labeled anti-rabbit IgG (Sigma-Aldrich). Bands were visualized using Lumi Light plus Western blotting detection system (Roche Diagnostic, Germany) and Hyperfilm ECL (Amersham Biosciences, UK).

5.1.6 Whole Lung Histological Analysis

Lungs were fixed by inflation with 4% paraformaldehyde overnight and dehydrated in 70% ethanol. Tissue was embedded in paraffin wax, 3 μm thick sections were prepared and stained with Masson's trichrome to measure collagen deposition. Percentage of fibrosis in the lung was evaluated by light microscopy by three different qualified persons using a blinded system.

5.1.7 Immunohistochemical Analysis in Lung Tissue

Dewaxed and rehydrated lung tissue sections were subjected to endogenous peroxidase inactivation with a blocking reagent (DakoCytomation, Denmark) for 10 min. They were then incubated for two hours with a 1/50 dilution in PBS of mouse anti-human α-SMA monoclonal antibody (DakoCytomation) that cross-reacts with mouse α-SMA. Next, sections were incubated for 1 hour with a peroxidase-labeled polyclonal rabbit anti-mouse immunoglobulin (DakoCytomation). Peroxidase activity was visualized using DAB+ Chromogen (DakoCytomation) as substrate and sections were counterstained with Harris hematoxylin. Expression of αSMA was evaluated by light microscopy and expressed as percentage of α-SMA positive area.

Lymphocyte infiltrate in the lungs was also determined by immunohistochemical analysis. In this case, lung sections were incubated with a mouse anti-human αCD3 monoclonal antibody that cross-reacts with mouse CD3 (NeoMarkers, CA) and then with an anti-mouse immunoglobulin coupled with peroxidase (DakoCytomation). CD3-positive cells were counted in a whole lobe (about 20 fields).

5.1.8 Statistical Analysis

Comparisons of data among experimental groups were performed using the nonparametric Mann-Whitney rank-sum test. Statistical significance was considered at $P<0.05$.

Figure 7:
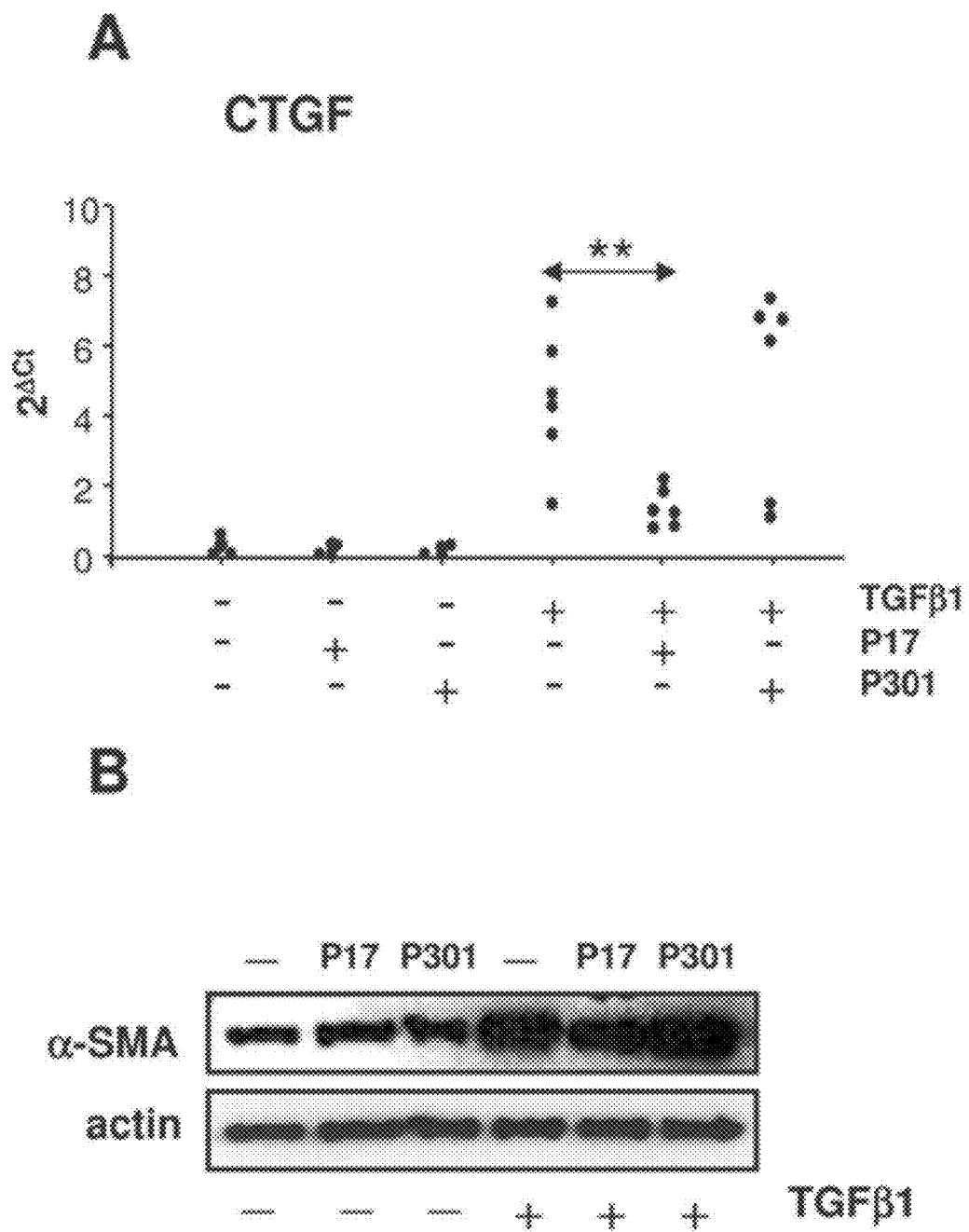
FIG. 7 shows that P17 (SEQ ID NO: 17) inhibits Connective Tissue Growth Factor (CTGF) and alpha-Smooth Muscle Actin (α-SMA) expression induced by Transforming Growth Factor (TGF)-β1 in IMR-90 lung fibroblasts. IMR-90 cells were cultured with 5 ng/ml of TGFβ1 and treated with or without P17 or control peptide P301 (100 μg/ml). After 6 hours, CTGF mRNA expression was determined by RT-PCR (A) Results represent the values of one out of two independent experiments (**, P<0.01). (B) IMR-90 cells were cultured as above and 24 hours later, α-SMA expression was determined by western blot. Results correspond to one out of three independent experiments.

5.2 Results 5.2.1 P17 Inhibits CTGF and αSMA Expression Induced by TGF-β1 in IMR-90 Cells Since CTGF is a mediator of TGF-β1 actions, the in vitro effect of P17 on the expression of CTGF mRNA in IMR-90 cells was analyzed. FIG. 7A shows that in the absence of TGF-β1, CTGF is not induced. However, CTGF mRNA expression induced by TGF-β1 in IMR-90 cells was significantly decreased by P17 ($P<0.01$), but not by control peptide P301. Moreover, analysis of α-SMA expression by western blot in similar cultures showed that α-SMA induced by TGF-β1 in IMR-90 cells was also inhibited by P17 (FIG. 7B).

Figure 8:
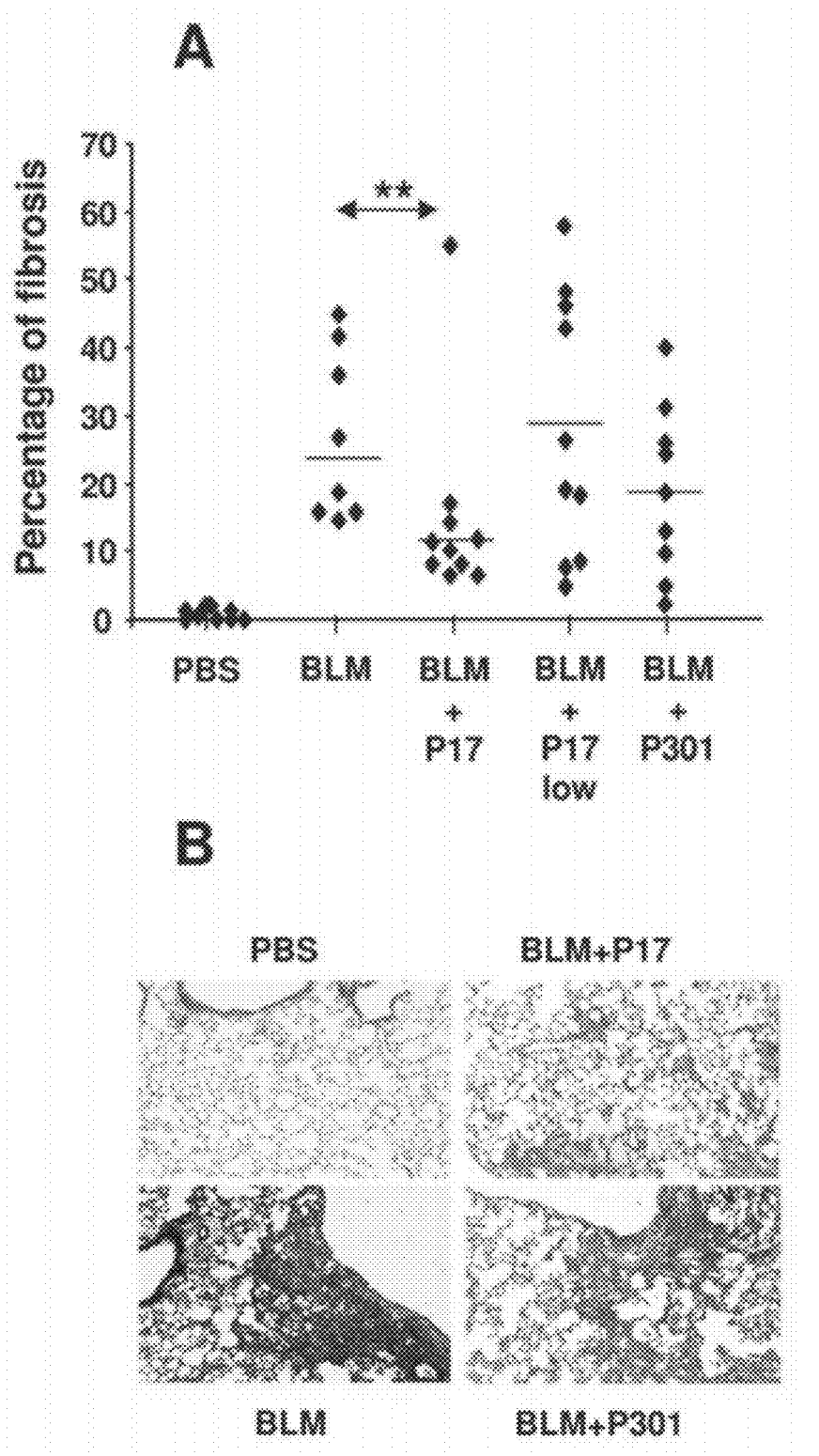
FIG. 8 shows the protective effect of P17 (SEQ ID NO: 17) in bleomycin-induced lung fibrosis (Example 5). Mice received a single bleomycin instillation to induce lung fibrosis or PBS as control of damage. Two days later, bleomycin-instilled mice were treated with or without peptides at alternate days for a total period of 24 days: PBS; bleomycin (BLM); bleomycin plus treatment with P17 (75 μg/mouse) (BLM+P17); bleomycin plus treatment with low doses of P17 (25 μg/mouse) (BLM+P17 low); bleomycin plus treatment with control peptide P301 (75 μg/mouse) (BLM+P301). (A) Percentage of fibrosis 26 days after bleomycin instillation was evaluated by light microscopy in lung sections with Masson's Trichrome stain. Horizontal bars correspond to mean. The results are representative of two independent experiments (**, P<0.01). (B) Representative pathologic findings of lung tissue from mice treated as indicated. Photomicrographs are shown at a magnification of 10×.

5.2.2 P17 Prevents the Development of Bleomycin-Induced Lung Fibrosis and Myofibroblast Accumulation Findings obtained in vitro with IMR-90 fibroblasts prompted inventors to study if P17 had an in vivo effect on the prevention of bleomycin-induced lung fibrosis in mice. It was found that mice treated intraperitoneally with a dose of 75 μg/mouse of P17 two days after bleomycin instillation, showed a significant decrease of fibrosis ($P<0.01$) at day 26, as compared with control peptide-treated mice (FIG. 8). No beneficial effect was observed in mice treated with a lower dose of P17 (25 μg/mouse).

Figure 9:
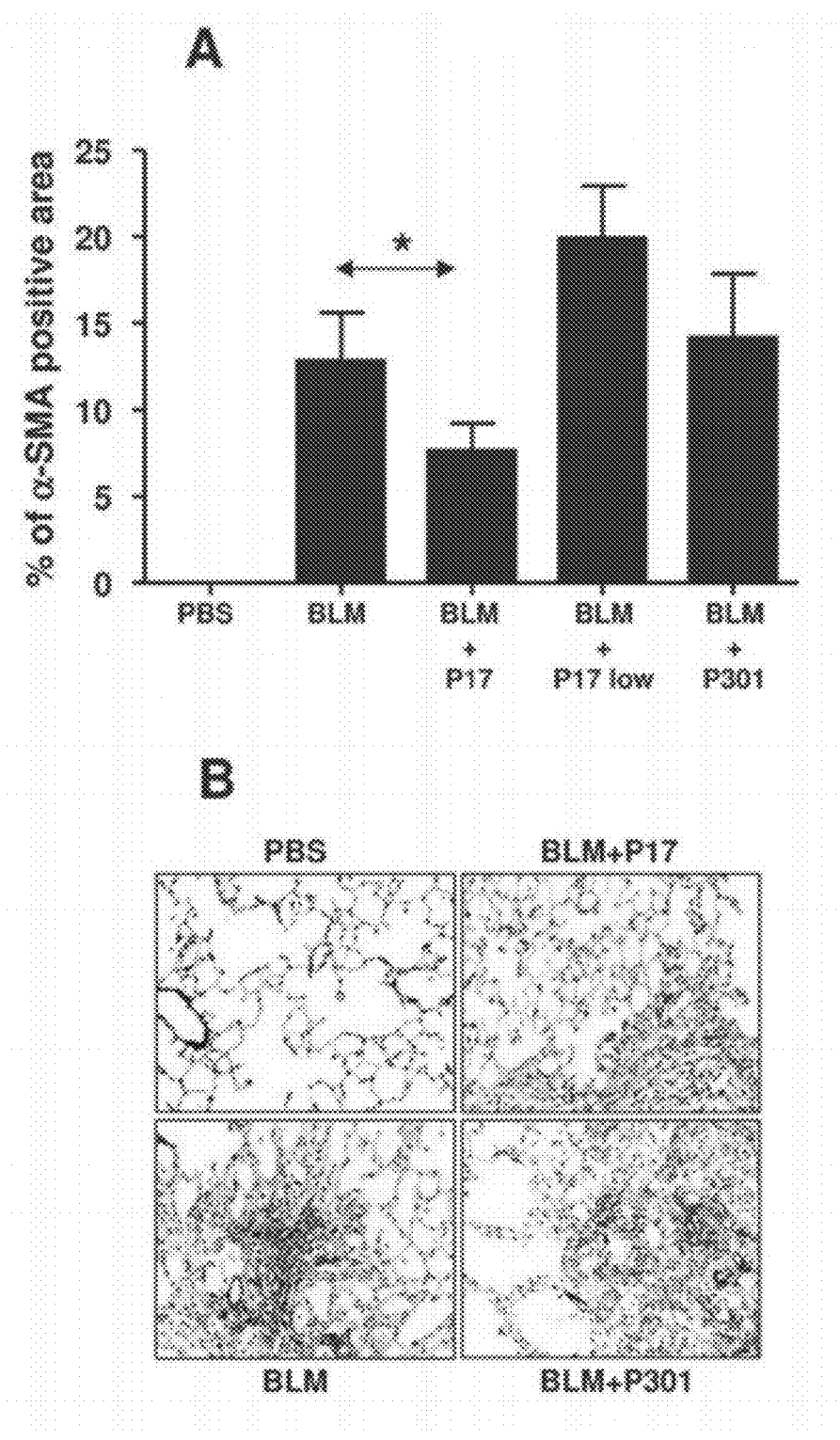
FIG. 9 shows that P17 (SEQ ID NO: 17) attenuates the presence of myofibroblast foci in bleomycin-induced lung fibrosis (see Example 5). Immunohistochemical detection of alpha-Smooth Muscle Actin was evaluated in lung sections of mice from FIG. 2. (A) (*, P<0.05). Data are expressed as mean±SEM. (B) Representative hematoxylin counterstained sections shown at a magnification of 10×.

Immunohistochemical analysis revealed fewer areas of myofibroblasts (as determined by expression of α-SMA) in lungs from mice treated with the high dose of P17 ($P<0.05$) than in lungs from mice treated with the low dose of P17 or from P301-treated mice (FIG. 9).

Figure 10:
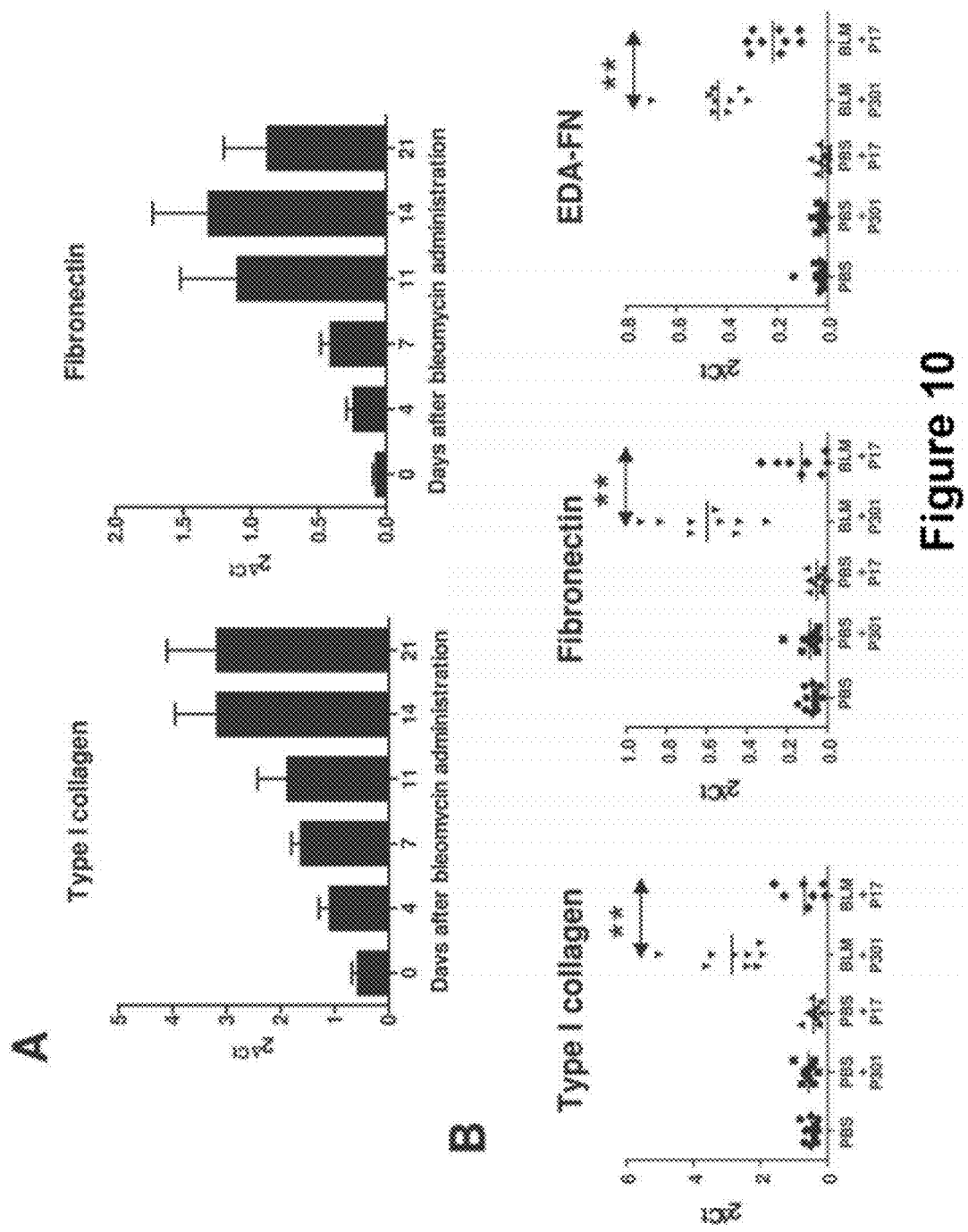
FIG. 10 shows that P17 (SEQ ID NO: 17) downregulates collagen type I, fibronectin and extra domain A of fibronectin (EDA-FN) mRNA expression in bleomycin-induced lung fibrosis. (A) Time course analysis of the expression of collagen type I and fibronectin mRNA after bleomycin instillation. (B) mRNA expression of collagen type I, fibronectin and EDA-FN in lung tissue from PBS-instilled mice with or without P17 or control peptide P301 (75 μg/mouse), and from bleomycin-instilled mice treated with P17 or P301. The levels of mRNA were evaluated by RT-PCR. Histone 3 mRNA was used as internal control. Horizontal bars correspond to mean. (**, P<0.01).

5.2.3 P17 Downregulates Expression of Type I Collagen, Fibronectin and Extra Domain A of Fibronectin in Lungs from Mice with Pulmonary Fibrosis Since TGF-β1 is a potent in vitro stimulator of extracellular matrix (ECM) proteins, inventors investigated the effect of P17 on the expression of mRNA encoding collagen type I and fibronectin genes, in lungs from mice with bleomycin-induced PF and treated with P17 as described above. Bleomycin instillation markedly increased mRNA expression of these genes between days 7 and 14 (FIG. 10A). Inventors thus studied their expression 14 days after bleomycin instillation. A significant reduction in the levels of mRNA encoding collagen type I ($P<0.01$) was observed in mice treated with P17 (FIG. 10B). Similarly, fibronectin mRNA levels were also significantly downregulated in P17-treated mice ($P<0.01$) (FIG. 10B). EDA-FN, a fibronectin isoform expressed during wound healing and fibrotic changes, which is necessary for the induction of the myofibroblast phenotype by TGF-β1, showed also lower expression levels in the lungs of mice treated with P17, as compared to mice treated with control peptide ($P<0.01$) (FIG. 10B).

5.2.4 Effect of P17 on Lung Lymphocyte Infiltrate and Cytokine Production

Figure 11:
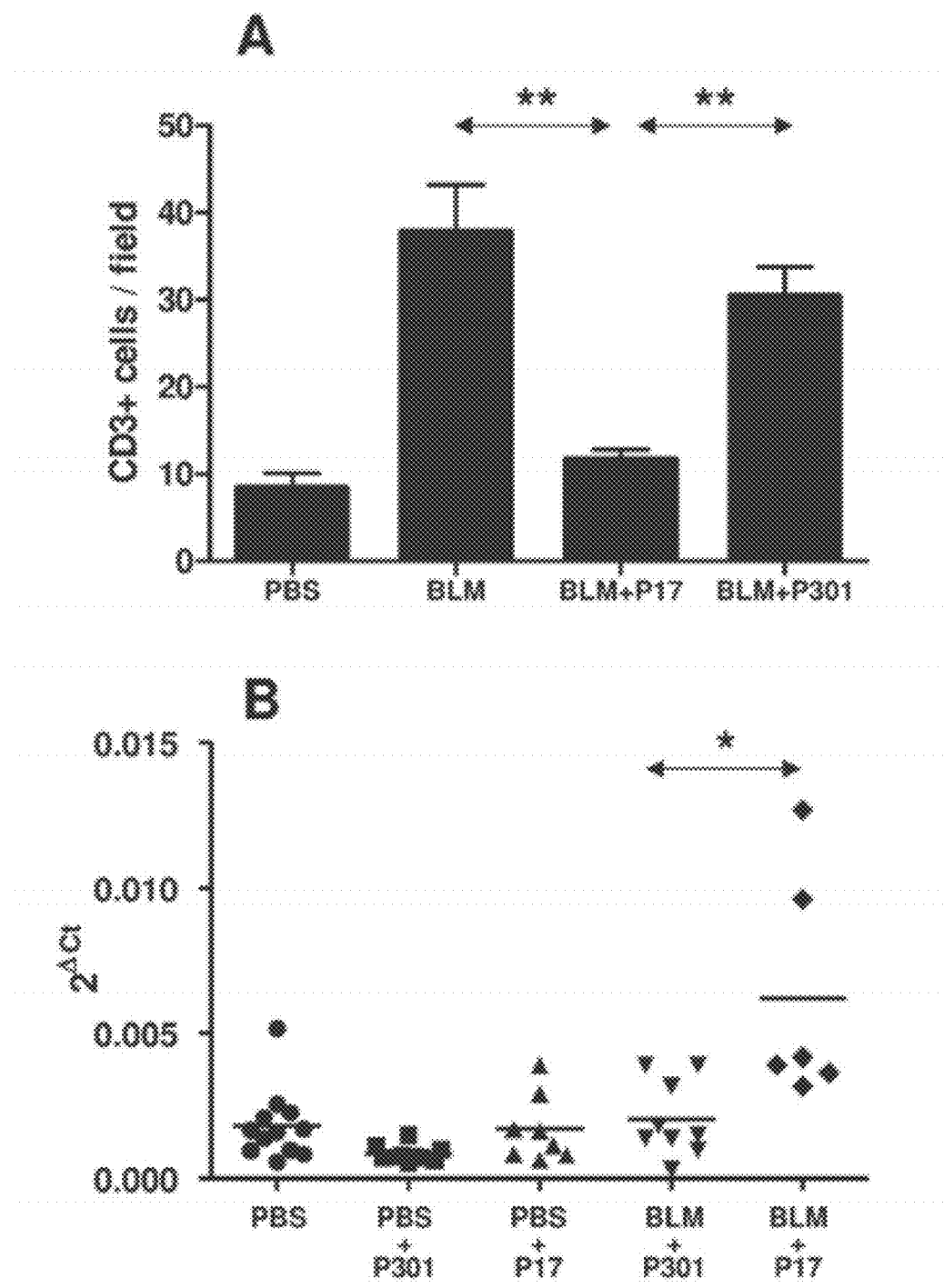
FIG. 11 shows that the effect of P17 (SEQ ID NO: 17) on lung lymphocyte infiltrate and interferon-gamma (IFN-γ) expression in mice with bleomycin-induced pulmonary fibrosis. (A) Immunohistochemical detection of CD3$^+$ cells in lung sections from PBS-instilled mice (PBS) (n=5), bleomycin-instilled mice (BLM) (n=6), and bleomycin-instilled mice treated with P17 (BLM+P17) (n=6) or control peptide P301 (BLM+P301) (n=4) (75 μg/mouse in both groups). CD3 positive cells were counted in 20 different fields. Data are expressed as mean±SEM. (**, P<0.01) (B) IFN-γ mRNA expression in lung tissue from PBS-instilled mice treated with or without P17 or control P301 or from bleomycin instilled mice treated with P17 or control peptide P301 (75 μg/mouse). mRNA levels were evaluated by RT-PCR using Histone 3 mRNA as internal control. Horizontal bars correspond to mean. (*, P<0.05).

Due to the role that inflammatory cells play in the outcome of PF, immunohistological analysis of lung sections was carried out to measure T lymphocytes at sites of inflammation. It was found that bleomycin-instilled mice treated with P17 two days after bleomycin administration, showed a significant reduction ($P<0.01$) of T lymphocytes as compared with bleomycin-instilled mice administered with or without control peptide P301 (FIG. 11A).

The inflammatory infiltrate in bleomycin-induced PF is characterized by a T helper type 2 (Th2) cytokine profile which enhances fibrogenesis. Thus, cytokine mRNA expression in lungs from bleomycin-induced PF and treated with P17 was measured. RT-PCR analysis of these samples did not show any significant difference in the expression of IL-10 or IL-4 mRNA in mice treated with P17 or P301 control peptide (data not shown). However, IFN-γ mRNA expression was upregulated in lungs from mice treated with P17 ($P<0.05$) (FIG. 11B).

5.2.5 Therapeutic Effect of P17 in Mice with Bleomycin-Induced Lung Fibrosis

Figure 12:
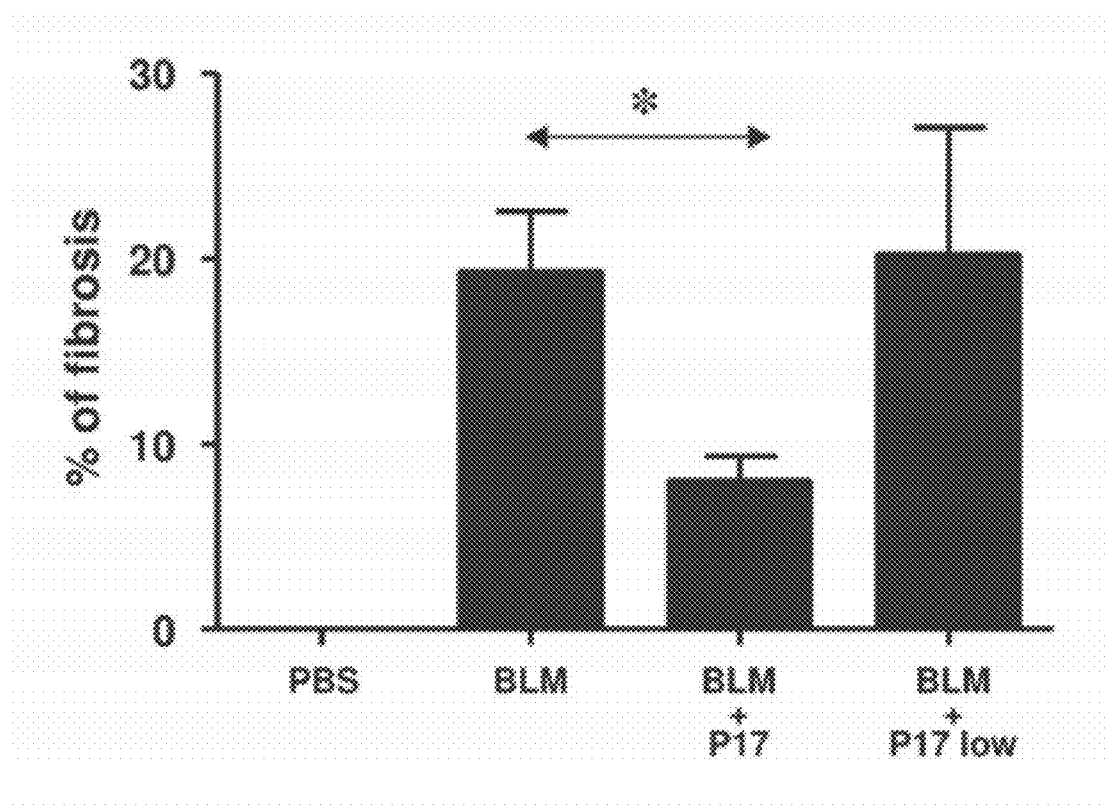
FIG. 12 shows the therapeutic effect of P17 (SEQ ID NO: 17) in bleomycin-induced lung fibrosis. Lung fibrosis was induced in mice by a single instillation of bleomycin and 10 days later, when fibrosis was established, mice were treated daily with P17 at 75 μg/mouse (n=8) or P17 at a lower dose (25 μg/mouse; n=7) for 16 days or left untreated (n=17). PBS-instilled mice (n=10) were included as control of damage. Fibrosis was evaluated by light microscopy in lung sections with Masson's Trichrome stain 26 days after bleomycin instillation. Values correspond to mean±SEM, and they are representative of two different experiments. (*, P<0.05).

Due to the preventive effect of P17 administration in the outcome of bleomycin-induced fibrosis, inventors decided to study the therapeutic effect of P17 when fibrosis is already established. To this end, inventors started daily P17 administration 10 days after bleomycin instillation, a time point when lung fibrosis can be observed. Interestingly, a significant attenuation of fibrosis ($P<0.05$) was found at day 26 in mice treated with P17 (75 μg/mouse), as compared with untreated mice. No beneficial effect was observed when mice were treated with a lower dose (25 μg/mouse) of P17 (FIG. 12).

5.3 Discussion

TGF-β1 is characterized by its potent profibrotic effect. Indeed, it has been demonstrated its direct contribution to wound healing and lung fibrosis. Thus, inventors hypothesized that P17, which has shown to be an inhibitor of TGF-β1 both in vitro and in vivo [Dotor J et al., Identification of peptide inhibitors of transforming growth factor beta 1 using a phage-displayed peptide library. Cytokine 2007; 39:106-115] might have a beneficial effect on the development of bleomycin-induced lung fibrosis in mice. In this example, it has been shown that in vitro, expression of CTGF, a gene induced by TGF-β1 which plays an important role in the development of fibrosis, is down-regulated by P17 in the human lung fibroblast IMR-90 cell line. It has been also observed that P17 reduces fibroblast differentiation into myofibroblasts by the attenuation of the α-SMA expression induced by TGF-β1. Interestingly, inventors had previously determined that P17 decreased Smad2 phosphorylation induced by TGF-β1 in these lung fibroblasts [Dotor et al., supra], indicating that the down-regulation of the expression of these genes mediated by P17 is due to a specific inhibition of TGF-β1 signaling.

In addition to in vitro results, inventors have seen in vivo that P17 has a preventive effect in bleomycin-induced lung fibrosis in mice. This beneficial effect on fibrosis development observed in lung sections from mice treated with P17 was strengthened by a decrease of myofibroblasts in areas of fibrosis. These cells are crucial in the progression of the disease, being responsible for the accumulation of high levels of ECM proteins in the lung and the consistent tissue retraction. Moreover, one of the major effects of TGF-β1 described during the last years is the induction of expression of genes encoding ECM proteins. Inventors studies demonstrate that the histological effect of P17 treatment on bleomycin-induced PF correlates with a lower expression of collagen type I, fibronectin and EDA-FN mRNA. It has been also observed that preventive treatment with P17 inhibits differentiation of fibroblasts into myofibroblasts. These findings suggest that P17 may play a pivotal role in the inhibition of fibroblasts differentiation into myofibroblasts in lung pathologies.

For most pulmonary fibrotic diseases it has been found that an early inflammation phase after injury leads to the fibrotic process. In these pathologies, an exaggerated physiological mechanism of tissue repair is often associated with this severe fibrosis. In this Example, it has been observed that lungs from P17-treated mice showed a lower number of lymphocytes in areas of extensive inflammation. Some authors have shown that TGF-β1 can induce T lymphocyte migration in vitro and suggest that this factor may attract lymphocytes to sites of inflammation [Adams et al. Transforming growth factor-beta induces human T lymphocyte migration in vitro. J. Immunol. 1991; 147:609-612]. If that was the case, TGF-β1 neutralization with P17 could reduce the lymphocyte infiltrate. In the pathogenesis of lung fibrosis contradictory results have been reported concerning the role that Th1 and Th2 cytokines play on the development of the disease. Although an increase of the Th1 cytokine IFN-γ in bleomycin induced lung fibrosis has been reported [Chen E S et al. Attenuation of lung inflammation and fibrosis in interferon-gamma-deficient mice after intratracheal bleomycin. Am J Respir Cell Mol Biol 2001; 24:545-555], others describe that an immune response dominated by Th1-cytokines prevents the development of fibrosis [Oldroyd S D et al. Interferon-gamma inhibits experimental renal fibrosis. Kidney Int 1999; 56:2116-2127]. In contrast, a Th2-cytokine response induces fibroblast activation [Gharaee-Kermani M et al. Lung interleukin-4 gene expression in a murine model of bleomycin-induced pulmonary fibrosis. Cytokine 2001; 15:138-147]. In the inventors experiments, bleomycin administration does not upregulate IFN-γ expression. However, mice treated with P17 after bleomycin administration, have an increased expression of IFN-γ mRNA in their lungs, without differences in IL-10 and IL-4. In P17-treated mice, IFN-γ might inhibit fibroblast proliferation and production of collagen, as previously reported in in vivo studies [Kim J H et al. Natural killer T (NKT) cells attenuate bleomycin-induced pulmonary fibrosis by producing interferon-gamma Am J Pathol 2005; 167:1231-1241]. According to the inventors results, it has been described that IFN-γ attenuates lung fibrosis, and inhibitors of lung fibrosis are able to increase IFN-γ level. Moreover, clinical trials administering IFN-γ have been designed for the treatment of PF [Raghu G et al. A placebo-controlled trial of interferon gamma-1b in patients with idiopathic pulmonary fibrosis. N Engl J Med 2004; 350:125-133]. Thus, it is suggested that P17 may also have a beneficial effect in the attenuation of PF by modifying the cytokine profile in the lungs.

As mentioned above, TGF-β1 is not only important at early phases of fibrosis development, but it may also have a role when fibrosis is already established. Therefore, the effect of P17 was also analyzed when administered 10 days after bleomycin instillation. In this case, P17 was able to significantly attenuate lung fibrosis measured 26 days after bleomycin instillation. This inhibitory effect of P17 is particularly interesting, since most TGF-β1 inhibitors used to treat PF in animal models have shown their effects by previous or simultaneous administration to bleomycin instillation, a time-point before fibrosis is established, but few data [Tabata C et al. Thalidomide prevents bleomycin-induced pulmonary fibrosis in mice. J Immunol 2007; 179:708-714] are available concerning treatment of established fibrosis. Moreover, this therapeutic model may resemble more the relevant clinical setting of PF, suggesting that patients with established PF might also benefit from the use of this inhibitory peptide.

In conclusion, peptide inhibitor of TGF-β1 P17 has shown activity in vitro and in vivo, as demonstrated in preventive and therapeutic models of bleomycin-induced PF in mice. Thus, these results suggest that P17 may be of potential interest in the treatment of pulmonary fibrotic disorders.

EXAMPLE 6

Treatment of Corneal Fibrosis and Haze

TGF-β1 is one of the main fibrosis induction mediators. Fibrosis in cornea causes loss of transparency, tissue contraction and scar transformation, thus causing corneal haze. This Example was focused on studying corneal fibrosis in experimental animals and its complete or partial decrease after the topical administration of TGF-β1 inhibitor peptides: p17 (SEQ ID NO: 17) and p144 (SEQ ID NO: 51).

6.1 Materials and Methods 6.1.1 Corneal Damage Induction
Animal Fibrosis Model

In this study, domestic hens (*Gallus gallus domesticus*) aged between 12 and 16 months were initially used as experimental animals but due to the difficulty of the model, especially in relation to obtaining and handling the animals, it was decided to use Long-Evans rats. Furthermore, it was bibliographically verified that these animals are used for in vivo models for studying corneal fibrosis because they allow following the evolution of the damage with more precision since they are pigmented rats and, like humans, have a Bowman's membrane.

Experimentation Groups

Male Long-Evans rats aged 10 weeks were used, divided into 5 groups:

Group 1: 12 rats, 6 treated with dexamethasone and 6 treated with mitomycin C

Group 2: 12 rats, 6 treated with p17 of the first formulation (see section 6.1.2.b) and 6 treated with p144 of the first formulation (see section 6.1.2.b)

Group 3: 12 rats, 6 treated with p17 of the second formulation (see section 6.1.2.b) and 6 treated with p144 of the second formulation (see section 6.1.2.b)

Group 4: 12 rats, 6 treated with p17 of the third formulation (see section 6.1.2.b) and 6 treated with p144 of the third formulation (see section 6.1.2.b)

Group 5: 12 rats, 6 treated with p17 of the fourth formulation (see section 6.1.2.b) and 6 treated with p144 of the fourth formulation (see section 6.1.2.b)

Group 6: 12 rats, 6 treated with p17 of the fifth formulation (see section 6.1.2.b) and 6 treated with p144 of the fifth formulation (see section 6.1.2.b)

To perform the damage in the cornea, the animals were anesthetized with isoflurane and a 5 mm Whatman paper disc impregnated in 1 N NaOH for 30 seconds was applied to them in the central part of the eye. After the damage, they were washed with abundant physiological saline serum and an antibiotic ointment was applied to them to prevent possible infections in the affected area.

After conducting several in vivo studies with the previously described groups of animals, it could be concluded that the chemical damage occurring after the application of NaOH for 30 seconds caused an excessive lesion for the study which was to be conducted, therefore it was decided to conduct new experiments reducing the time to 15 seconds.

6.1.2 Treatment

First, an experiment was conducted to corroborate the clinical efficacy of the drugs usually used in the treatment of corneal fibrosis: dexamethasone and mitomycin C. In said first experiment, it was observed that the obtained results did indeed correspond to those described in the scientific literature. For this reason and from that time onwards, the following studies were conducted with groups of animals treated exclusively with p17 and p144. It was thus possible to work with a larger number of animals, thus obtaining more significant results.

a) Summary of the Posology:

| Treatment | Time of Treatment |
|---|---|
| First Week | |
| Peptides (1 drop) | 8:30 |
| Antibiotic ointment | 13:00 |
| Peptides (1 drop) | 18:00 |
| Second-Sixth Week | |
| Peptides (1 drop) | 8:30 |
| Peptides (1 drop) | 18:00 |

It was randomly established that the left eye of each animal would act as a control and that the right eye would be the treated eye, such that the same animals acts as a control in addition to being treated. It must be pointed out that all the animals received antibiotic treatment in both eyes daily only during the first week of the study for the purposes of avoiding microbial keratitis.

b) Formulation of the Eye Drops:

One of the objectives of this study was to achieve the most suitable formulation to achieve clinical results similar to those obtained with dexamethasone and mitomycin C. To that end, the different formulations listed below were tested:

First Formulation

2% Carbopol (1 g in 50 ml) heated at 60° C. and sonicated in MQ water filtered with a 0.45 μm filter p144 and p17 at a final concentration of 1 mg/ml 10 mg were weighed and sonicated in 5 ml of 2% carbopol at 4° C. over the weekend until the use thereof on Tuesday Note: The formulations were maintained at 4° C. throughout the study.

Second Formulation

The carbopol solution was prepared as follows: 40 ml at 1.5% carbopol-2001 sonicated and centrifuged 5 min 2000 rpm (bubbles)+400 μl of triethanolamine (99%) and 1.2 ml 1N HCl (stirred and centrifuged)

p144: 1 ml of carbonate+10 mg of p144. Sonicate. 9 ml of carbopol solution were added and sonication p144 control: the same but without p144 p17: 10 ml of the carbopol solution+10 mg of p17. Sonicate p17 control: carbopol solution Note: The carbonate raises the pH of the carbopol solution, increasing the viscosity. All the solutions were gel in water. The formulations were maintained at 4° C. throughout the study.

Third Formulation

The carbopol solution was prepared as follows: 40 ml at 1.5% carbopol-2001 sonicated and centrifuged 5 min 2000 rpm (bubbles)

p144: 1 ml of carbonate+10 mg of p14. Sonicate. 9 ml of carbopol solution were added and sonication p144 control: the same but without p144 p17: 10 ml carbopol solution+10 mg of p17. Sonicate p17 control: carbopol solution Note: Adjustment of viscosity by adding triethanolamine (10-20 μl) and HCl (32%) (2-10 up until obtaining a suitable viscosity. The formulations were maintained at 4° C. throughout the study.

Fourth Formulation

Starting from 23 mg/ml Healon 5™ (AMO) sodium hyaluronate in PBS, a dilution was performed until obtaining a final concentration of 1 mg/ml of hyaluronate. A 0.6 ml syringe of 23 mg/ml HLNC until 14 ml of PBS and carbonate:

p144: 14 mg were dissolved in 7 ml of carbonate with 1 mg/ml of HLNC. Sonicate p17: 4 mg were dissolved in 7 ml of PBS with 1 mg/ml of HLNC Note: The formulations were maintained at 4° C. throughout the study.

Fifth Formulation

Starting from 0.15% sodium hyaluronate (Hyabak 10 mL, Thea) without preservatives:

p144: 20 mg were dissolved in 5 ml of eye drops, 40 μl of saturated concentrated NaOH were incorporated, stirring and adding in portions of 5 μl. It was sonicated until solubilization. To adjust the pH, 500 μl of 1M Hepes were added, such that the pH changed from 10.5 to 7 p144 control: 40 μl of saturated NaOH and 500 μl of 1 M HEPES (final concentration of HEPES 50 mM)

p17: 20 mg were dissolved in 5 ml of the eye drops, it was sonicated until complete solubilization and it was incorporated to the vial with a 10 ml syringe and a blue needle to perforate the filter of the contained (final concentration 2 mg/ml)

p17 control: non-manipulated eye drops

Note: The formulations were maintained at 4° C. throughout the study.

After all the in vivo studies conducted on the different groups (section 6.1.1) it was determined that the most suitable formulation to attempt reversing the damage generated with 1 N NaOH was the fifth formulation. Therefore, all the results shown in relation to in vivo will refer to this type of treatment.

6.1.3 Weekly Follow-Up of the Corneal Lesions a) Semi-Quantitative Analysis by Means of Corneal Biomicroscopy The administration of the treatment was initiated twenty-four hours after the damage. After that time a follow-up of the damage was performed, which consisted of taking photographs at days 0, 7, 14, 21, 28 and 35. To take the photographs the animals were anesthetized with isoflurane. Photographs were taken of both the control eye (left) and of the treated eye (right) with and without fluorescein. The photographs with fluorescein allowed to observe the evolution of the epithelial closure of the generated lesion, whereas the photographs without fluorescein show the evolution of the haze of the lesioned area. The photographs without fluorescein were taken first. These photographs were taken with the white color filter of the camera. Then, the photographs with fluorescein were taken such that a drop of commercial fluorescein (Colircusi Fluorescein) was added on the eye for 60 seconds. After that time, the area was washed with physiological saline and the eyes were photographed in darkness and using the blue filter of the camera.

b) Quantitative Analysis of Corneal Haze

This analysis allowed to obtain numerical area values from the study conducted in section 6.1.3.a). To that end, the ImageJ program was used in which both the total area of the eye of each animal and the damaged area were measured. In order to be able to carry out comparable measurements, the damaged area was divided by the total area. Thus, the error due to differences in the size of the eyes between different animals or the differences in relation to the perspective with which the photograph is taken was minimized. All the data obtained were referred to the initial value obtained with the photographs at day 0, the initial damage in all the animals was thus considered to be 100%.

6.1.4 Sacrifice of the Animals and Enucleation of the Eyes

The animals were sacrificed by neck dislocation after having been anesthetized with isoflurane. After the sacrifice, the enucleation was performed and the eyes were placed for 24 hours in Davidson's solution for the purpose of fixing them. After this time, the eyes of the animals were passed from Davidson's solution to 4% formol, 24 hours later the eyes were passed to 70% ethanol, where they can remain up to one month.

6.1.5 Inclusion of the Tissue in Paraffin

The fixed tissues, which were in 70% ethanol, were dehydrated so that they could be included in paraffin. Once included, the samples can be cut to 3-5 μm in the microtome and subsequently the corresponding histological and immunohistochemical analysis can be conducted.

6.1.6 Histological Analysis of the Sections

Initially, the decision was made to study the samples at immunohistochemical level by means of using fibrosis markers such as α-SMA or fibronectin, quantify the amount of collagen after the staining with Sirius Red and quantify the number of inflammatory cells. However, it was not possible to carry out most of these techniques due to problems with the choice of the suitable antibody because there are not many specific antibodies against rats. Furthermore, by consulting other research centers (IOVA, Valladolid (Spain)) it was seen that it was convenient to quantify the efficacy of the peptides in the inhibition of corneal fibrosis in a more refined manner by means of molecular signaling studies.

Therefore, Western Blot and immunofluorescence studies were conducted to determine, from cells extracted from the in vivo studies, the signaling pathway used by the peptides administered topically. It should be emphasized that said studies were conducted on fibroblasts from rabbit cornea and not from rat cornea. This decision was made due to the difficulty entailed in isolating fibroblasts from rodent eyes.

6.1.7 Statistical Study of the Data

The comparison of the obtained results was performed by means of the Student's t-test for related samples using the SPSS 15.0 software.

6.2. Results 6.2.1 In Vivo Results

Figure 13:
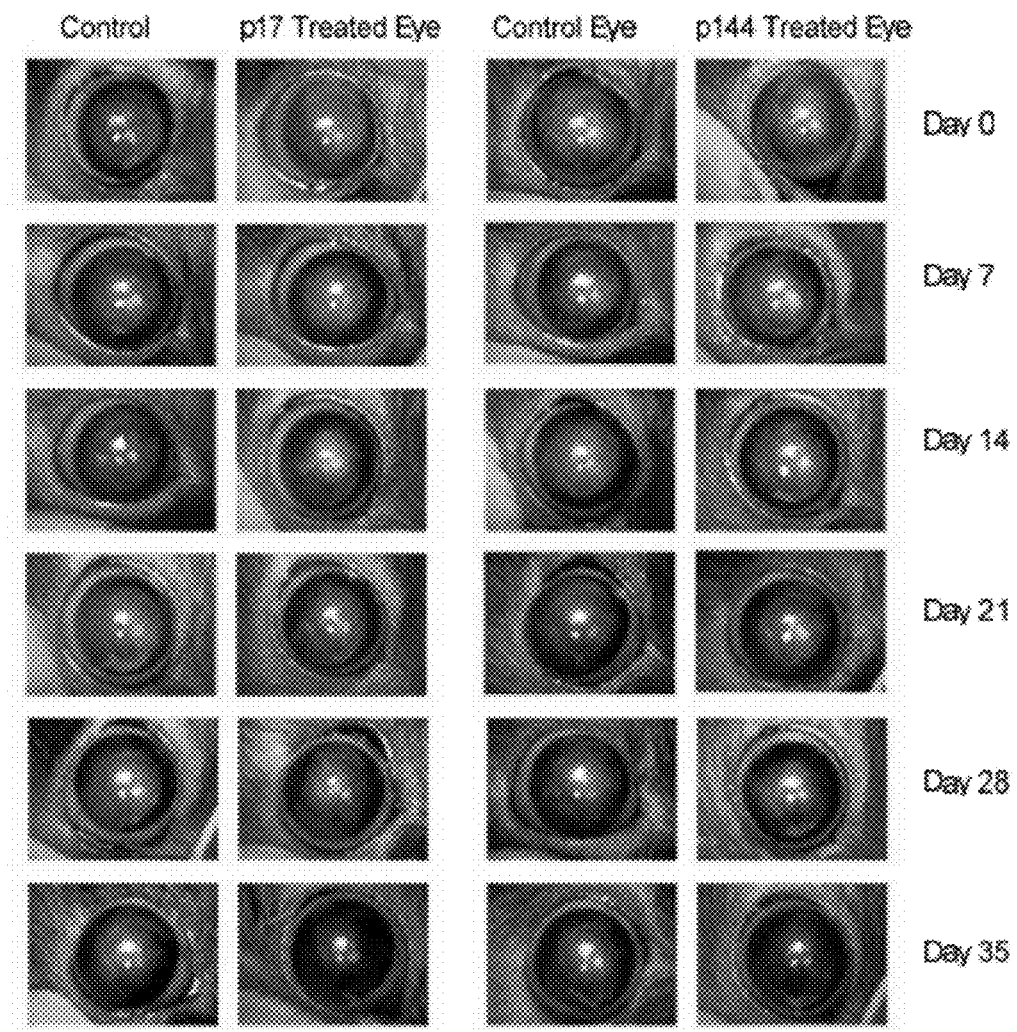
FIG. 13 shows the evolution of the effect of TGF-β1 inhibitor peptides (p17 and p144) on corneal haze.
Figure 14:
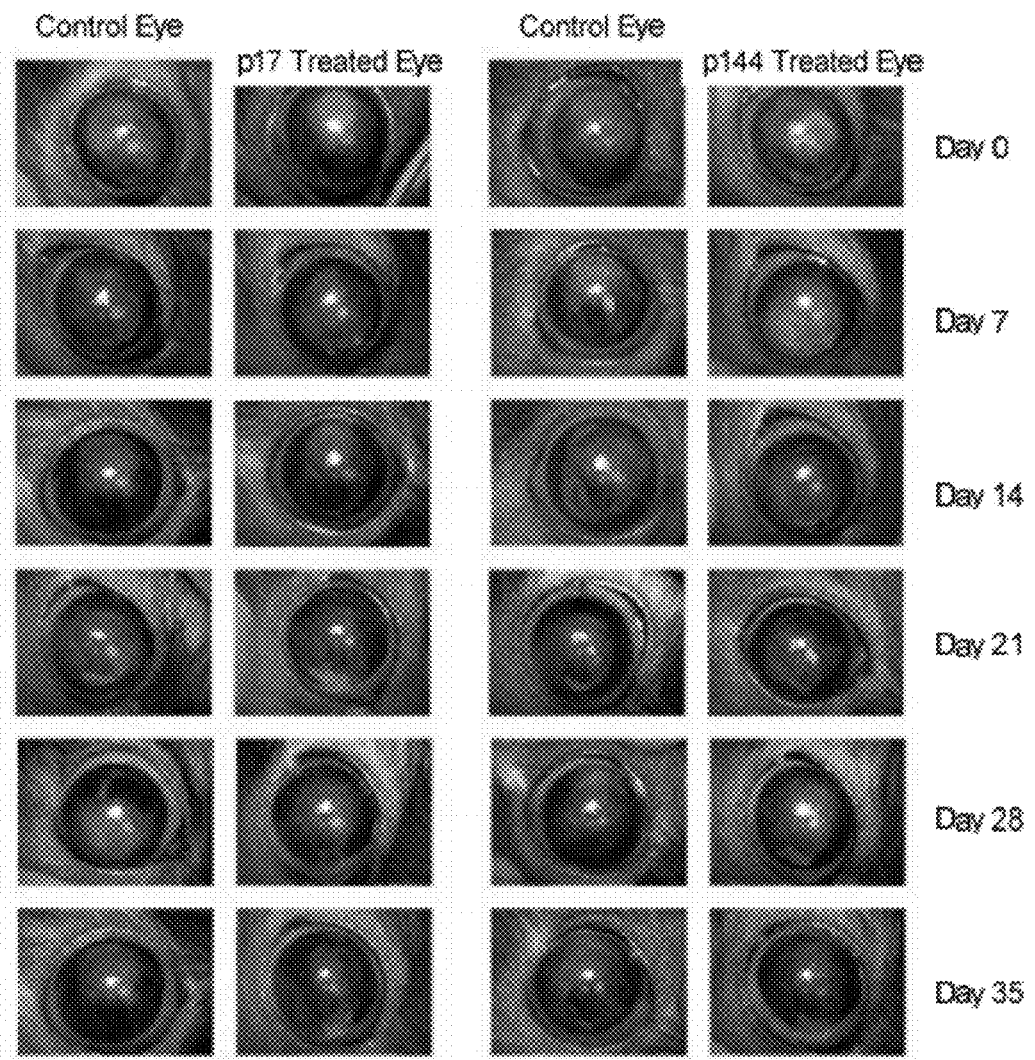
FIG. 14 shows the evolution of the effect of peptides p17 and p144 on epithelial closure.
Figure 15:
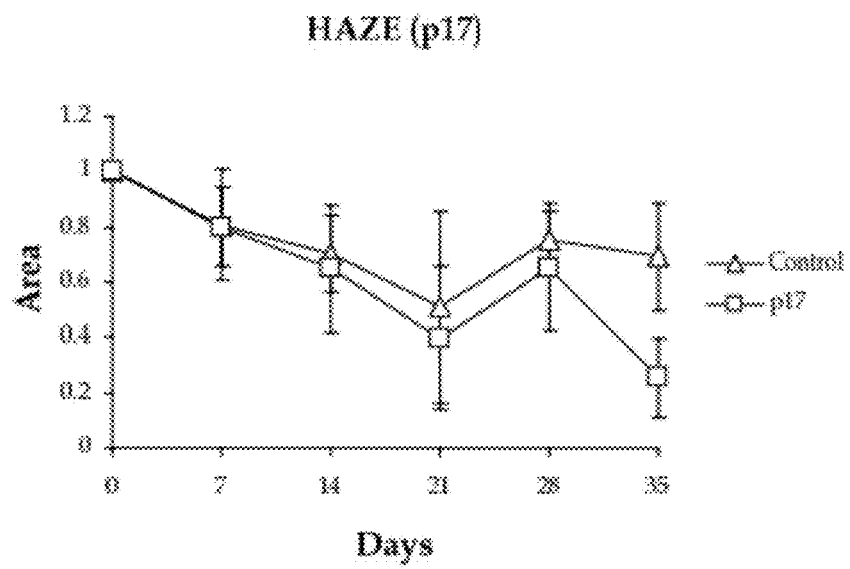

The results obtained in the different groups of animals are shown below. A clear decrease of the haze (FIG. 13) and of the epithelial closure (FIG. 14) in the eyes treated with peptide, both p17 and p144, with respect to the control, can be seen.

After analyzing the images with ImageJ program a series of area data were obtained from which the graphs shown in FIGS. 15, 16, 17 and 18 were made. Said graphs show the mean±the standard deviation of all the animals (n=12) of each group at days 0, 7, 14, 21, 28 and 35.

6.2.2 Biochemical Results a) Western Blot Studies

Since the scientific literature repeatedly describes the TGF-β1 signaling pathways, the decision was made to go into depth in such pathways by means of the techniques described in the methodology section. Said pathways involve the study of the Smad protein family, specifically the study of the isoforms Smad2, 2/3 and 7.

To that end, protein extracts obtained from the primary culture of rabbit fibroblasts were treated with TGF-β1 at concentrations of 0, 3 and 5 ng/ml and, 50 and 200 μg/ml of peptide p17 and p144.

Expression of p-Smad2

Decrease of the activation of p-Smad2 after the application of the inhibitory peptide p17 (FIG. 19) was not observed, whereas with p144 a slight inhibition of the expression of p-Smad2 after the treatment with 50 μg/ml was observed. The inhibition is greater with the treatment of 200 μg/ml reaching the values of the controls (FIG. 19).

Expression of Smad 2/3

The expression of Smad 2/3 in the primary culture was not affected with the treatment of TGF-β1 or with the inhibitory peptides p17 and 144 (FIG. 20). FIG. 20 shows the inhibitory peptide p17 in the first place and the action of the p144 in the second place.

Expression of Smad 7

The expression of Smad 7 in the primary culture of rabbit fibroblasts was not affected with the treatment of TGF-β1 or with the inhibitory peptides (FIG. 21).

b) Immunofluorescence Studies

Treatment with TGF-β1

The application of 3 and 5 ng of TGF-β1 induced the translocation of p-Smad2 to the nucleus (stained green) [FIG. 22].

Treatment with TGF-β1 Inhibitor Peptides (p17 and p144)

Treatment with p17 did not inhibit the translocation of p-Smad2 to the nucleus but it was inhibited by treatment with p144, which indicates that this peptide inhibits the TGF-β1 signaling pathway in the primary culture of rabbit corneal fibroblasts (FIG. 23).

6.3 Conclusions

Treatment of the chemical lesions induced after corneal damage with 1N NaOH in the different experimentation groups decreases significantly after the treatment with p17 and p144, which undoubtedly has an extraordinary clinical importance.

Additionally, the results obtained show that:

the most suitable formulation for the treatment of the lesions made with 1N NaOH was the fifth formulation (comprising sodium hyaluronate);

treatment with p17 or with p144 during the six-week assay period significantly reversed the initial damage generated with NaOH in relation to haze and epithelial closure;

TGF-β1 activates the phosphorylation of Smad2 in the primary culture of rabbit corneal fibroblasts but does not modify the levels of Smad2/3 and Smad7. The latter are not modified after treatment with p17 or p144;

treatment with p17 does not have any effect on the signaling cascade of TGF-β1 in the primary culture of rabbit corneal fibroblasts, which shows a discrepancy with the results obtained in the in vivo studies; a non-binding explanation leads to thinking that the signaling pathway used by p17, which shows great effectiveness in the animal models studied, is not mediated by the proteins studied in this work but by other different ones from the Smad2, Smad2/3 and Smad7 proteins; and treatments with p144, at concentrations of 50 µg/ml and 200 µg/ml block the TGF-β1 transduction signal, inhibiting the phosphorylation of Smad2 and therefore its subsequent translocation to the nucleus; these findings are perfectly correlated with the results found in the in vivo studies and suggest that the intracellular effects are mediated by the Smad2 pathway.

The invention claimed is:

1. A method of treating pulmonary fibrosis which comprises administering to a subject in need of treatment a therapeutically effective amount of a peptide capable of binding to TGF-β1 and inhibiting the biological activity of TGF-β1, or a pharmaceutically acceptable salt thereof,
wherein said peptide is a peptide selected from the group consisting of:
a peptide whose amino acid sequence comprises SEQ ID NO: 17;
a peptide whose amino acid sequence comprises SEQ ID NO: 33;
a peptide whose amino acid sequence comprises SEQ ID NO: 34; and
a peptide whose amino acid sequence comprises SEQ ID NO: 53.

2. The method according to claim 1, wherein said peptide is a peptide whose amino acid sequence is SEQ ID NO: 17.

3. The method according to claim 1, wherein said peptide comprises an amino acid sequence selected from the group consisting of SEQ ID NO: 33 and SEQ ID NO: 34, and their pharmaceutically acceptable salts.

4. The method according to claim 1, wherein said peptide comprises an amino acid sequence selected from the group consisting of SEQ ID NO: 17, SEQ ID NO: 33, and SEQ ID NO: 34, and their pharmaceutically acceptable salts.

5. The method according to claim 1, wherein said peptide is a peptide whose amino acid sequence is SEQ ID NO: 33.

6. The method according to claim 1, wherein said peptide is a peptide whose amino acid sequence is SEQ ID NO: 34.

7. The method according to claim 1, wherein said peptide is a peptide whose amino acid sequence is SEQ ID NO: 53.

* * * * *